United States Patent [19]

Brewster et al.

[11] Patent Number: 5,053,415

[45] Date of Patent: Oct. 1, 1991

[54] PYRIDINE DERIVATIVES

[75] Inventors: Andrew G. Brewster, Macclesfield; George R. Brown, Wilmslow; Alan W. Faull, Macclesfield; Reginald Jessup, Hankelow; Michael J. Smithers, Macclesfield, all of England

[73] Assignee: Imperial Chemical Industries plc, London, England

[21] Appl. No.: 424,611

[22] Filed: Oct. 20, 1989

[30] Foreign Application Priority Data

Oct. 21, 1988 [GB] United Kingdom ............... 8824667
Oct. 21, 1988 [GB] United Kingdom ............... 8824668
Aug. 18, 1989 [GB] United Kingdom ............... 8918937

[51] Int. Cl.$^5$ .................... C07D 451/06; A61K 31/46
[52] U.S. Cl. .................................... 514/336; 514/333; 514/278; 546/268; 546/256; 546/283; 546/284; 546/15
[58] Field of Search ............... 514/333, 336; 546/268, 546/256, 284, 285

[56] References Cited

U.S. PATENT DOCUMENTS

| 4,554,011 | 11/1985 | Loh | 71/88 |
| 4,567,197 | 1/1986 | Brewster | 514/452 |
| 4,735,963 | 4/1988 | Matassa | 514/433 |
| 4,736,057 | 4/1988 | Guildford | 560/59 |
| 4,755,684 | 10/1988 | Smithers | 514/452 |
| 4,831,046 | 5/1989 | Brown | 514/381 |
| 4,921,866 | 5/1990 | Brewster et al. | 514/336 |

FOREIGN PATENT DOCUMENTS 0201352 11/1986 European Pat. Off. .
0329360 8/1989 European Pat. Off. .

Primary Examiner—Mary C. Lee
Assistant Examiner—Peter Davis
Attorney, Agent, or Firm—Cushman, Darby & Cushman

[57] ABSTRACT

The invention concerns novel, pharmaceutically useful 1,3-dioxane alkenoic acid derivatives of the formula I containing a pyridyl moiety at position 4 of the dioxane ring and in which the groups at positions 2, 4 and 5 have cis-relative stereochemistry, X is hydrogen, alkoxy or hydroxy, Y is vinylene, n is 1 or 2, $A^1$ is alkylene, the substituents $R^1$ and $R^2$ at position 2 of the dioxane ring have a variety of values defined hereinafter, and $R^4$ is hydroxy, a physiologically acceptable alcohol residue or alkanesulphonamido, and the pharmaceutically acceptable salts thereof. The invention also includes processes for the manufacture and use of the acid derivatives as well as pharmaceutical compositions for therapeutic use in one or more of a variety of diseases such as ischaemic heart disease, cerebrovascular disease, asthmatic disease and/or inflammatory disease.

13 Claims, No Drawings

PYRIDINE DERIVATIVES

This invention concerns novel pyridine containing alkenoic acid derivatives and, more particularly, it concerns novel 1,3-dioxan-5-yl alkenoic acids containing a pyridyl moiety attached at position 4 of the 1,3-dioxane ring. The alkenoic acids of the invention have valuable pharmaceutical properties and the invention includes pharmaceutical compositions containing the novel acids and processes for the manufacture and medical use of said novel acids.

It is known that the arachidonic acid metabolite thromboxane $A_2$ (hereinafter referred to as "$TXA_2$") is a powerful vasoconstrictor and a potent aggregator of blood platelets. $TXA_2$ is also a potent constrictor of bronchial and tracheal smooth muscle. $TXA_2$ may therefore be involved in a variety of disease conditions, for example ischaemic heart disease such as myocardial infarction, angina, cerebrovascular disease such as transient cerebral ischaemia, migraine and stroke, peripheral vascular disease such as atherosclerosis, microangiopathy, hypertension and blood clotting defects due to lipid imbalance.

It is believed that $TXA_2$ exerts its physiological action through the thromboxane receptor, via which receptor various other prostanoid contractile substances derived from arachidonic acid, such as prostaglandins $H_2$, $F_2$ alpha and prostaglandin $D_2$, can exert contractile effects. There are two principal ways in which the effects of $TXA_2$ can be ameliorated. The first is by administering a pharmacological agent which preferentially occupies the thromboxane receptor, but yet does not produce the contractile effects which follow the binding of $TXA_2$ (or of prostaglandins $H_2$, $F_2$ alpha and/or $D_2$). Such an agent is said to possess $TXA_2$ antagonist properties. The second way is to administer a pharmacological agent which inhibits one or more of the enzymes involved in the production of $TXA_2$ and in particular which inhibits the enzyme known as thromboxane synthase ($TXA_2$ synthase). Such an agent is said to be a $TXA_2$ synthase inhibitor. Accordingly, it may be seen that agents which possess $TXA_2$ antagonist properties and which inhibit $TXA_2$ synthase may be expected to be of therapeutic value in the treatment of one or more of the above mentioned diseases or other diseases in which $TXA_2$ is involved. Also, agents which possess $TXA_2$ antagonist properties may be expected to be of value additionally in treating those diseases in which prostaglandins $H_2$, $F_2$ alpha and/or $D_2$ are involved, for example especially in treating asthmatic and inflammatory diseases. Although 1,3-dioxane $TXA_2$ antagonists are known (for example, in European patent, publication number 94239B1), as are certain $TXA_2$ synthase inhibitors (for example, in European patent application, publication number 98690A2), obtaining compounds which combine both properties to a useful extent is not straightforward.

However, we have now discovered (and this is the basis for our invention) that, surprisingly, certain 1,3-dioxan-5-yl alkenoic acids of the formula I (set out, together with the other chemical structures, at the end of this specification) containing a pyridyl moiety attached to position 4 of the 1,3-dioxane ring, are good inhibitors of $TXA_2$ synthase and also possess significant $TXA_2$ antagonist properties and are useful pharmaceutical agents.

According to the invention there is provided a 1,3-dioxane alkenoic acid derivative of the formula I (set out hereinafter together with the other chemical formulae in Roman numerals) wherein: n is the integer 1 or 2; X is hydrogen, hydroxy or (1–4C)alkoxy; Y is methyleneoxy, vinylene or ethylene; $A^1$ is (1–6C)alkylene; and a) $R^2$ is hydrogen; and $R^1$ is naphthyl or phenylthio(1–6C)alkyl, optionally bearing 1 or 2 substituents selected from halogeno, cyano, nitro, (1–4C)alkyl, (1–4C)alkoxy and trifluoromethyl, or $R^1$ is a group of the formula $R^3.A^2$—, in which:

$R^3$ is phenyl bearing a substituent which is selected from (1–4C)alkyl, (1–4C)alkoxy, hydroxy, (2–5C)alkenyl, (1–4C)alkylthio, (1–4C)alkylsulphinyl, (1–4C)alkylsulphonyl, (2–5C)alkanoyl, carboxy, [(1–4C)alkoxy]carbonyl, [N-(1–4C)alkyl]carbamoyl, (1–5C)alkanoylamino and (1–4C)alkyl itself bearing a (1–4C)alkoxy, cyano, carboxy or [(1–4C)alkoxy]carbonyl, and the phenyl optionally bearing a second substituent selected from (1–4C)alkyl, (1–4C)alkoxy, halogeno, trifluoromethyl, nitro and cyano;

or $R^3$ is thienyl or furyl optionally bearing 1 or 2 substituents independently selected from halogeno, (1–4C)alkyl, nitro and cyano; and $A^2$ is (1–6C)alkylene, oxy(1–6C)alkylene or (2–6C)alkenylene, up to three carbon atoms of any of which may be wholly or partially fluorinated, or $A^2$ is a direct bond to $R^3$;

or $R^1$ is a group of the formula $Q^2.A^3.Q^1$—, in which:

$Q^1$ and $Q^2$ are aromatic moieties, one of which is a benzene moiety and the other of which is a benzene, pyridine or naphthalene moiety, any of which may optionally bear a substituent selected from halogeno, cyano, nitro, (1–4C)alkyl, (1–4C)alkoxy and trifluoromethyl, and $A^3$ is oxy, thio, sulphinyl, sulphonyl, carbonyl, carbamoyl, iminocarbonyl, ureido, (1–6C)alkylene, oxy(1–6C)alkylene, (2–6C)alkenylene or a direct bond between $Q^1$ and $Q^2$;

(b) $R^1$ is pentafluoroethyl and $R^2$ is hydrogen, or both $R^1$ and $R^2$ are trifluoromethyl; or (c) $R^1$ and $R^2$ are both independently alkyl or together form alkylene, such that $R^1$ and $R^2$ together contain 5–9 carbon atoms; and $R^4$ is hydroxy, a physiologically acceptable alcohol residue, or (1–4C)alkanesulphonamido;

or a pharmaceutically acceptable salt thereof.

It will be appreciated that the compounds of formula I possess asymmetric carbon atoms and may exist and be isolated in racemic and optically active forms. The invention includes both the racemic forms and any optically active form (or mixtures thereof) which is capable of antagonising one or more of the actions of $TXA_2$ and inhibiting the synthesis of $TXA_2$, it being well known in the art how to prepare individual optical isomers (for example by synthesis from optically active starting materials or resolution of a racemic form) and how to determine the $TXA_2$ antagonist properties and $TXA_2$ synthase inhibitory properties using one or more of the standard tests referred to hereinafter.

It will be understood that the groups at positions 4 and 5 (and position 2, when $R^2$ is hydrogen) of the 1,3-dioxane moiety of formula I have cis-relative stereochemistry, as have the groups adjacent to Y when it is vinylene (i.e. the latter compounds exist as the "Z" isomer). Further, although a particular configuration is shown in the chemical formulae attached hereto, this does not necessarily correspond to the absolute configuration.

It is to be understood that the generic term "alkylene" includes both straight chain and branched chain alkylene groups such as ethylene and ethylidene and other generic terms are to be construed similarly. However, when a specific term such as "butyl" is used, it is specific to the straight chain or "normal" butyl group, branched chain isomers such as "t-butyl" being referred to specifically when required.

Particular values for $R^1$ and $R^2$ when they are alkyl include, for example, methyl, ethyl, propyl, isopropyl, butyl and pentyl; and when together they form alkylene include, for example, tetramethylene, pentamethylene and hexamethylene, any of which may optionally bear 1 or 2 methyl substituents.

A particular value for $R^1$ when it is phenylthio(1-6C)alkyl is, for example, 1-methyl-1-(phenylthio)ethyl or phenylthiomethyl, optionally substituted as defined hereinabove.

Particular values for substituents which may be present on $R^1$ when it is naphthyl or phenylthio(1-6C)alkyl, or on the aromatic moieties $Q^1$ or $Q^2$ as defined above include, for example: for (1-4C)alkyl: methyl and ethyl; for (1-4C)alkoxy: methoxy and ethoxy; and for halogeno: fluoro, chloro and bromo. A particular value for X when it is alkoxy is, for example, methoxy or ethoxy.

Particular values for substituents which may be present when $R^3$ is phenyl, thienyl or furyl as defined above include, for example: for (1-4C)alkyl: methyl and ethyl; for (1-4C)alkoxy: methoxy and ethoxy; for halogeno: fluoro, chloro and bromo; for (2-5C)alkenyl: vinyl, 2-propenyl and 3,3-dimethylpropenyl; for (1-4C)alkylthio: methylthio and ethylthio; for (1-4C)alkylsulphinyl: methylsulphinyl and ethylsulphinyl; for (1-4C)alkylsulphonyl: methylsulphonyl and ethylsulphonyl; for (2-5C)alkanoyl: acetyl, propionyl, butyryl and 2-oxopropyl; for [(1-4C)alkoxy]carbonyl: methoxycarbonyl, ethoxycarbonyl and t-butoxycarbonyl; for [N-(1-4C)alkyl]carbamoyl: N-methylcarbamoyl, N-ethylcarbamoyl and N-propylcarbamoyl; for (1-5C)alkanoylamino: formamido, acetamido and propionamido; and for substituted (1-4C)alkyl: methyl, 1-ethyl, 2-ethyl, or 1-, 2- or 3-propyl, bearing a (1-4C)alkoxy (such as methoxy or ethoxy), cyano, carboxy or [(1-4C)alkoxy]carbonyl (such as methoxycarbonyl or ethoxycarbonyl) substituent.

Particular values for $R^4$ when it is a physiologically acceptable alcohol residue are those which render the subsequent ester biodegradable and are chosen from, for example, (1-6C)alkyl optionally bearing a hydroxy or (1-4C)alkoxy substituent, such as methyl, ethyl, 2-hydroxyethyl, 2-methoxyethyl, propyl or 3-hydroxypropyl; phenyl; and benzyl; the latter two of which may bear 1 or 2 optional substituents selected from halogeno (such as fluoro, chloro, bromo or iodo), (1-4C)alkyl (such as methyl or ethyl) and (1-4C)alkoxy (such as methoxy or ethoxy).

Particular values for $R^4$ when it is (1-4C)alkanesulphonamido include, for example, methanesulphonamido, ethanesulphonamido and butanesulphonamido.

Particular values for $A^1$ when it is (1-6C)alkylene include, for example: methylene, ethylene, trimethylene, tetramethylene and 1,1-dimethylethylene) and 1,1-dimethyltrimethylene, of which values ethylene and trimethylene are generally preferred, ethylene being particularly preferred.

Particular values for $A^2$ when it is (1-6C)alkylene include, for example, (1-4C)alkylene (such as methylene, ethylene, trimethylene, isopropylidene and 1,1-dimethylethylene) and 3,3-pentylidine; when it is (2-6C)alkenylene include, for example, vinylene, 1,3-propenylene and 1,4-buten-2-ylene; and when it is oxy(1-6C)alkylene include, for example, oxymethylene, oxytetramethylene (i.e. a group of the formula: —O.(CH$_2$)$_4$—), 1-oxy-1-methylethyl (i.e. a group of the formula: —O.C(CH$_3$)$_2$—) and 2-oxy-1,1-dimethylethyl (i.e. a group of the formula —O.CH$_2$.C(CH$_3$)$_2$—), it being understood that the oxy link is to the group $R^3$ and not to the 1,3-dioxane ring.

Particular values for $A^2$ when it contains fluoro substituents include, for example, when it is difluoromethylene or 2,2,2-trifluoro-1-oxy-1-trifluoromethylethyl (i.e. a group of the formula: —O.C(CF$_3$)$_2$—).

A particular value for $R^3$ when it is thienyl or furyl is, for example, 2-thienyl, 3-thienyl or 2-furyl, optionally bearing 1 or 2 substituents independently selected from methyl, ethyl, chloro, bromo, nitro and cyano.

$Q^1$ is preferably a benzene moiety and $Q^2$ is typically a benzene, pyridine or napthalene moiety, optionally substituted as defined above.

Particular values for $A^3$ when it is (1-6C) alkylene include, for example, (1-4C)alkylene (such as methylene, ethylene, trimethylene, isopropylidene and 1,1-dimethylethylene) and pentamethylene; when it is (2-6C)alkenylene include, for example, vinylene, 1,3-propenylene and 1,4-buten-2-ylene; and when it is oxy(1-6C)alkylene include, for example, oxymethylene, oxyethylene and oxytetramethylene (i.e. a group of the formula: —O.(CH$_2$)$_4$—), it being understood that the oxy link may be to $Q^1$ or $Q^2$.

A generally preferred value for n is 1, for X is hydrogen, for Y is cis-vinylene, for $A^1$ is ethylene and for $R^4$ is hydroxy.

Specific values for $R^1$ and $R^2$ include, by way of example:

a) when $R^1$ and $R^2$ are both trifluoromethyl;

b) when $R^1$ is thienyl or furyl, optionally containing a halogeno, cyano or nitro substituent, and $R^2$ is hydrogen;

c) when $R^1$ is phenoxy(1-4C)alkyl (especially 1-methyl-1-phenoxyethyl), the phenyl moiety of which contains a first substituent selected from (1-4C)alkyl and (1-4C)alkoxy, optionally together with a second substituent selected from (1-4C)alkyl, (1-4C)alkoxy, halogeno, nitro, trifluoromethyl and cyano, and $R^2$ is hydrogen;

d) $R^1$ is phenylthio(1-4C)alkyl (especially 1-methyl-1-phenylthioethyl), the phenyl moiety of which optionally bears 1 or 2 substituents independently selected from (1-4C)alkyl, (1-4C)alkoxy, halogeno, nitro, trifluoromethyl and cyano, and $R^2$ is hydrogen;

e) when $R^1$ is naphthyl optionally bearing 1 or 2 substituents selected from halogeno, (1-4C)alkyl and nitro, and $R^2$ is hydrogen; and f) when $R^1$ is benzylphenyl, benzyloxyphenyl, (pyridylmethoxy)phenyl, (naphthylmethoxy)phenyl, phenoxyphenyl and (phenoxymethyl)phenyl.

A group of compounds of the invention of particular interest comprises compounds of formula II wherein: $R^4$ has the meanings defined above; $A^4$ is (1-4C)alkylene; $X^1$ is hydrogen or hydroxy; and $R^5$ is naphthyl or thienyl optionally bearing a substituent selected from cyano, nitro, halogeno and (1-4C)alkyl, or $R^5$ is a group of the formula $R^6.A^5$— in which: $R^6$ is phenyl bearing a first substituent selected from (1-4C)alkyl, (1-4C)alkoxy, hydroxy, (2-5C)alkenyl, (1-4C)alkylthio, (1-4C-

)alkylsulphinyl, (1–4C)alkylsulphonyl, (2–5C)alkanoyl, carboxy, [(1–4C)alkoxy]carbonyl, [N-(1–4C)alkyl]carbamoyl, (1–5C)alkanoylamino and (1–4C)alkyl, the latter bearing a (1–4C)alkoxy, cyano, carboxy or [(1–4C)alkoxy]carbonyl, said phenyl optionally bearing a second substituent selected from (1–4C)alkyl, (1–4C)alkoxy, halogeno, trifluoromethyl, nitro and cyano, and $A^5$ is (1–4C)alkylene, oxy(1–4C)alkylene or a direct bond to $R^5$; together with the pharmaceutically acceptable salts thereof.

Particular values for substituents which may be present as part of $R^5$ or $R^6$ include, for example, those given hereinabove for $R^1$. Particular values for $R^6$ include, for example, when it is phenyl bearing a first (1–4C)alkyl (especially methyl or ethyl), (1–4C)alkoxy (especially methoxy) or hydroxy substituent, optionally together with a second nitro, halogeno (especially fluoro, chloro or bromo) or trifluoromethyl substituent.

Particular values for $A^4$ include, for example, those defined above for $A^1$ when it is (1–4C)alkylene, for example, ethylene, trimethylene and 1,1-dimethylethylene, of which values, ethylene and trimethylene are generally preferred.

Particular values for $A^5$ include, for example, those defined above for $A^2$ when it is a direct bond, (1–4C)alkylene or oxy(1–4C)alkylene, such as a direct bond, isopropylidene and 1,1-dimethylethylene, 1-oxy-1-methylethyl (i.e. a group of the formula: —O.C(CH$_3$)$_2$—).

Specific values for $R^5$ include, for example, when it is 1-naphthyl, 2-naphthyl, 2-chloro-1-naphthyl, 2-thienyl, 3-thienyl, 5-cyano-2-thienyl, 5-bromo-2-thienyl, 4-bromo-2-thienyl, 4-chloro-2-thienyl, 5-chloro-2-thienyl, 2-furyl, 5-bromo-2-furyl, 1-(4-methoxyphenoxy)-1-methylethyl, 1-(4-tert-butylphenoxy)-1-methylethyl, 1-(2-methoxyphenoxy)-1-methylethyl, 1-(2-methylthiophenoxy)-1-methylethyl, 1-(4-methylthiophenoxy)-1-methylethyl, 1-(2-methylsulphonylphenoxy)-1-methylethyl, 1-(4-methylsulphonylphenoxy)-1-methylethyl, 1-methyl-1-(2-methylphenoxy)ethyl, 2-phenylthiophenyl, 2-phenylsulphonylphenyl, 2-biphenylyl, 2-benzoylphenyl, alpha,alpha-difluororobenzyl, 1-methyl-1-(4-methoxy-2-nitrophenoxy)ethyl, 1-methyl-1-(4-methyl-2-nitrophenoxy)ethyl, 1-methyl-1-(2-cyano-4-methylphenoxy)ethyl, 1-methyl-1-(4-chloro-2-cyanophenoxy)ethyl, 1-methyl-1-(2-cyano-4-methoxyphenoxy)ethyl, 1-methyl-1-(2-cyano-5-methylphenoxy)ethyl, 1-methyl-1-(2-nitrophenoxy)ethyl, 1-(2-hydroxyphenoxy)-1-methylethyl or (E)-2-methoxystyryl.

A further group of compounds of the invention of particular interest comprises compounds of formula III wherein $A^4$ is (1–4C)alkylene; $X^1$ is hydrogen or hydroxy; $A^6$ is oxy, thio, sulphonyl, carbonyl, carbamoyl, iminocarbonyl, (1–6C)alkylene, oxy(1–6C)alkylene or a direct bond to $Q^3$, $Q^3$ is benzene, pyridine or naphthalene; $R^7$ and $R^8$ are independently selected from hydrogen, halogeno, cyano, nitro, (1–4C)alkyl, (1–4C)alkoxy and trifluoromethyl; and $R^4$ has the meanings defined above; together with the pharmaceutically acceptable salts thereof.

Particular values for $A^4$ in the formula III compounds are, for example, as for the formula II compounds stated above.

Particular values for $A^6$ include, for example, those defined above for $A^3$ when it is (1–6C)alkylene or oxy(1–6C)alkylene, such as methylene, ethylene, isopropylidene and oxymethylene, as well as oxy, thio, sulphonyl, carbonyl, carbamoyl, iminocarbonyl, and a direct bond to $Q^3$.

Examples of particular values for $R^7$ or $R^8$ include, fluoro, chloro and bromo, for halogeno; methyl and ethyl, for alkyl; and methoxy and ethoxy, for alkoxy, as well as hydrogen, cyano, nitro and trifluoromethyl. $Q^3$ is typically phenyl or pyridyl.

Specific values for the group of the formula $R^8.Q^3.A^6$— in the formula III compounds include, for example, phenoxy, phenylthio, phenylsulphonyl, phenyl, benzoyl, benzyl, benzyloxy, 4-cyanobenzyloxy, 2-pyridylmethoxy, 3-pyridylmethoxy, 4-pyridylmethoxy, phenoxymethyl, 2-naphthylmethoxy, 2,5-dimethoxybenzyloxy, 4-nitrobenzyloxy and 3-cyanobenzyloxy.

Particularly preferred value for $R^4$ is hydroxy, for $X^1$ is hydrogen and for $A^4$ is ethylene.

Particular novel compounds of the invention are described in the accompanying Examples and are provided, together with their pharmaceutically acceptable salts, as a further feature of the invention. Of these compounds, those described in Examples 18, 19, 20, 46 and 48 are of particular interest and are provided together with their pharmaceutically acceptable salts, their physiologically acceptable biodegradable esters and (1–4C)alkanesulphonamides, as further features of the invention.

It will be appreciated that the compounds of formula I are amphoteric when $R^4$ is hydroxy or alkanesulphonamido and can form salts with acids as well as bases. Particular pharmaceutically acceptable salts therefore include, for example, alkali metal and alkaline earth metal salts, ammonium salts, salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide, and also salts with acids affording physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be manufactured by conventional procedures of organic chemistry well known in the art for the manufacture of structurally analogous compounds. Such procedures are provided as a further feature of the invention and are illustrated by the following representative procedures in which $R^1$, $R^2$, $R^4$, X, Y, $A^1$ and n have any of the meanings defined hereinbefore.

(a) A diol derivative of the formula IV wherein one of $T^1$ and $T^2$ is hydrogen and the other is hydrogen or a group of the formula—CRaRb.OH (wherein Ra and Rb are the same or different (1–4C) alkyl) is reacted with an aldehyde derivative of the formula $R^1$.CHO or an acetal, hemiacetal or hydrate thereof.

The latter aldehyde [or its hydrate, or its acetal or hemiacetal with a (1–4C)alkanol (such as methanol or ethanol)] may conveniently be present in an excess.

The reaction is generally performed in the presence of an acid such as hydrogen chloride, hydrogen bromide, sulphuric acid, phosphoric acid, methanesulphonic acid or p-toluenesulphonic acid, conveniently in the presence of a suitable solvent or diluent, such as dichloromethane, toluene, xylene or an ether, for example, tetrahydrofuran, dibutyl ether, methyl t-butyl ether or 1,2-dimethoxyethane, and at a temperature in the range, for example, 0° to 80° C.

Those starting materials of formula IV wherein $T^1$ and $T^2$ are both hydrogen may be obtained, for example, by mild, acid catalysed, hydrolysis or alcoholysis of the dioxane ring of a compound of formula V wherein one of Ra and Rb is hydrogen or (1-4C)alkyl (such as methyl or ethyl)and the other is (1-4C)alkyl, obtained by an analogous procedure to process (d) hereinbelow, for example as described in European patent application, Publication No. 94239. The hydrolysis or alcoholysis will normally be carried out at a temperature in range 10° to 80° C. using an aqueous mineral acid such as hydrochloric acid in an alkanol such as ethanol or 2-propanol or an ether (such as tetrahydrofuran) as solvent.

The starting materials of formula IV wherein one of $T^1$ and $T^2$ is hydrogen and the other is a group of the formula —CRaRb.OH are intermediates in the above-mentioned formation of the starting materials of formula IV wherein $T^1$ and $T^2$ are both hydrogen. However, said intermediates are not normally isolated or characterised.

Accordingly, the invention also provides a preferred modified procedure (b) of process (a) which comprises reacting a 1,3-dioxane of formula V wherein one of Ra and Rb is hydrogen, methyl or ethyl and the other is methyl or ethyl with an excess of an aldehyde of the formula $R^1$.CHO (or a hydrate, acetal or hemiacetal thereof) in the presence of an acid (such as one of those given above), conveniently at a temperature in the range, for example, 10° to 80° C. and, optionally in the presence of a suitable solvent or diluent (such as one of those given above).

In some cases, it is necessary to modify procedures (a) and (b) where the aldehyde of formula $R^1$.CHO is not particularly reactive or tends to form an acyclic hemiacetal when reacted with the compound of the formula IV or V, for example when pentafluoropropionaldehyde is used in the production of formula I compounds wherein $R^1$ is a pentafluoromethyl group. Thus, a further procedure (c) of the invention comprises reacting a compound of the formula IV wherein one of $T^1$ and $T^2$ is hydrogen and the other is alkanesulphonyl (especially methanesulphonyl) or arenesulphonyl (especially benzene- or toluene-sulphonyl) with an aldehyde of the formula $R^1$. CHO (or a hydrate, acetal or hemiacetal thereof) in the presence of an acid catalyst and under the same general conditions as given above for procedure (a), followed by base-catalysed cyclisation of the acyclic intermediate obtained, for example using an alkali metal carbonate or hydride such as potassium carbonate sodium hydride, in a suitable solvent or diluent (such as an ether described above) and at a temperature in the range, for example, 20°-50° C.

The necessary starting alkanesulphonyl or arenesulphonyl esters of formula IV defined above may be conveniently obtained from the corresponding diol of formula IV ($T^1=T^2$=hydrogen) by reaction with one molecular equivalent of the appropriate alkanesulphonyl or arenesulphonyl halide (such as methanesulphonyl chloride or p-toluenesulphonyl chloride) in a suitable solvent or diluent (such as an ether or dichloromethane) at or near ambient temperature and in the presence of a suitable base (such as triethylamine or pyridine).

(d) For those compounds of formula I in which Y is vinylene and $R^4$ is hydroxy, an aldehyde of the formula VI is reacted with a Wittig reagent of the formula: $R_3P=CH.A^1.CO_2^-M^+$ wherein R is (1-6C)alkyl or aryl (especially phenyl; which is preferred) and $M^+$ is a cation, for example an alkali metal cation such as the lithium, sodium or potassium cation.

The process in general produces the required compounds of formula I in which the substituents adjacent to the double bond have predominantly the preferred cis-relative stereochemistry i.e. as the "Z" isomer. However the process also produces generally small amounts of the analogous compounds having trans-relative stereochemistry (i.e. the "E" isomer) which may be removed by a conventional procedure such as chromatography or crystallisation.

The process may be conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, −80° C., but is conveniently performed at or near room temperature, for example in the range 0° to 35° C.

(e) For those compounds wherein X is hydroxy, a compound of the formula VII wherein P is a protected hydroxy group (including (1-4C)alkoxy), is deprotected by conventional means.

Examples of particularly suitable protected hydroxy groups include, for example, (1-4C)alkoxy (such as methoxy), benzyloxy, allyloxy, tetrahydropyran-2-yloxy, (1-4C)alkanesulphonyloxy (especially methanesulphonyloxy) and trialkylsilyloxy of up to 10 carbon atoms.

The deprotection conditions used necessarily depend on the nature of the protected hydroxy groups. The removal of specific hydroxyl protecting groups is well documented in standard organic chemistry books and such conventional procedures well known in the art are included within the processes of the invention. Thus, for example, specific groups may be removed as follows:

(1), allyl or tetrahydropyran-2-yl: by treatment with strong acid such as trifluoroacetic acid, at e.g. 10° to 40° C.; (2) trialkylsilyl (such as t-butyldimethylsilyl, which is preferred): by reaction with aqueous tetrabutylammonium fluoride or sodium fluoride conveniently in a suitable solvent or diluent, such as tetrahydrofuran, or t-butyl methyl ether, and generally at or near ambient temperature, e.g. in the range 10° to 35° C.; (3) alkanesulphonyl: by hydrolysis in the presence of a base (such as sodium or potassium hydroxide) in a suitable aqueous solvent [such as an aqueous (1-4C)alkanol] and at e.g. 0° to 60° C.; (4)alkyl: by treatment with an alkali metal thioalkoxide or diphenylphosphide (such as sodium thioethoxide in a solvent such as N,N-dimethylformamide at e.g. 50°-160° C., or lithium diphenylphosphide in a solvent such as methyl t-butyl ether or tetrahydrofuran at e.g. 0°-60° C.); or (5) benzyl: by palladium catalysed hydrogenolysis in an alkanol such as ethanol at or near ambient temperature and pressure or by use of an alkali metal such as sodium in liquid ammonia.

The invention also includes a further procedure (f) analogous to (e) by which a hydroxy group required as a substituent on $R^1$ is introduced by removal of a suitable protecting group [such as (1–4C)alkyl and especially methyl] is removed as a final step, for example, using the conditions referred to above for generation of a hydroxypyridyl group.

(g) An ester of the formula VIII wherein $R^9$ is (1–6C)alkyl (especially methyl, ethyl, propyl or t-butyl), phenyl or benzyl the latter two optionally bearing 1 or 2 halogeno, (1–C)alkyl or (1–4C)alkoxy substituents, is decomposed.

The decomposition may be carried out using any one or more of the conventional reagents and conditions well known in the art for converting esters to acids. Thus, for example, the decomposition may conveniently be performed by base catalysed hydrolysis, for example by using an alkali metal hydroxide such as lithium, potassium or sodium hydroxide in a aqueous system conveniently in the presence of a suitable solvent or diluent such as tetrahydrofuran, methanol, ethanol or t-butyl methyl ether and a temperature in the general range, for example, 10° to 60° C. and, conveniently, at or near ambient temperature. Alternatively, when $R^9$ is t-butyl, the decomposition may be carried out thermally by heating the compound of formula VIII at a temperature in the general range, for example, 80° to 150° C., alone or in the presence of a suitable diluent such as diphenylether or diphenylsulphone.

(h) For a compound of the formula I wherein Y is ethylene, a compound of the formula IX wherein $Y^2$ is vinylene or ethynylene is hydrogenated.

The hydrogenation is preferably carried out in the presence of a suitable catalyst such as a noble metal catalyst, for example, palladium or platinum metal conveniently on an inert support such as carbon, barium sulphate, barium carbonate or calcium carbonate, using hydrogen at a pressure of about 1–2 bar. The process is generally carried out in a suitable solvent or diluent, for example, a (1–4C)alkanol (such as methanol, ethanol or propanol) and at a temperature in the range, for example, 15° to 35° C.

The invention also includes a modification of the above procedure adapted to the production of those compounds of formula I in which Y is vinylene which comprises partially hydrogenating a compound of the formula IX in which $Y^2$ is ethynylene. In this modification, a suitable poisoned catalyst for example a Lindlar catalyst (such as palladium on calcium carbonate, poisoned with lead) is used with similar solvents and temperatures as in process (h).

(i) For a compound wherein Y is methyleneoxy, an alcohol of the formula X is reacted with an alkanoic acid derivative of the formula XI in which L is a leaving group for example halogeno (such as chloro, bromo or iodo), alkanesulphonyloxy (such as methanesulphonyloxy) or arenesulphonyloxy (such as benzene- or toluene-sulphonyloxy).

The process is preferably carried out in the presence of a suitable base, for example, an alkali metal alkoxide (such as sodium methoxide or ethoxide), hydride (such as sodium hydride) or alkane derivative (such as butyl lithium) and in a suitable solvent or diluent, for example in a (1–4C)alkanol when an alkali metal alkoxide is used, in N,N-dimethylformamide or an ether, such as tetrahydrofuran or t-butyl methyl ether, when an alkali metal hydride is used, or in an ether when an alkane derivative is used. The process is generally carried out at a temperature in the range, for example, 0° to 50° C. In many cases it is preferred to preform a salt of the alcohol of formula X by reaction with the appropriate base and then react this salt with the alkanoic acid derivative of the formula XI in a suitable solvent or diluent such as one of those referred to above. It will be apparent that, when substituent X is hydroxy, it is generally necessary to protect such a substituent with a suitable hydroxy protecting group (for example as mentioned in process (e) above) before carrying out process (i) and then to remove the protecting group using analogous conditions to those in process (e) above.

The necessary starting materials for use in the above processes (a)–(i) may be obtained by general procedures well known for the production of structurally related compounds, for example using analogous procedures to those described in European patent no. 94239B1 and patent application no. 98691A2. The aldehydes of the formula VI may be obtained, for example, as shown in Schemes 1 and 2 hereinafter and as illustrated in the Examples. Alternatively, when a particular enantiomer is required, it may be obtained starting from a specific enantiomer of a 3-[2-(1-hydroxy-1-pyridylmethyl)pent-4-enyl]oxazolidin-2-one of the formula XIV in which $R^{10}$ is (1–4C)alkyl (especially isopropyl) itself obtained from aldol condensation of the corresponding 3-(4-pentenoyl)oxazolidin-2-one with pyridylcarboxaldehyde, as shown in Scheme 3 hereinafter.

The protected hydroxy derivatives of formula VII may be obtained for example by carrying out process (a) or (b) above with a suitable compound analogous to the 1,3-dioxane of formula V but in which X is a suitably protected hydroxy group, such a compound being itself readily obtainable using standard procedures analogous to those described above and to those set out in the accompanying Examples.

The appropriate diols of formula IV for the production of dioxanes of formula I or V wherein the pyridyl moiety bearing X and the alkenoic acid side-chain have cis-relative stereochemistry, may be obtained, for example, using an analogous procedure to that described in European patent application, publication no. 142323, starting from the appropriate pyridine-carboxaldehyde and succinic anhydride and a suitable base, such as that used for the aldol condensation of part (ii) of Scheme 3.

The esters of formula VIII may be made, for example, by carrying out process (a) using the appropriate ester of the diol corresponding to formula IV. Those compounds of formula IX in which $Y^2$ is ethynylene may be made, for example, as shown in Scheme 4 hereinafter. The alcohols of formula X may be obtained from the corresponding allyl compounds of formula XII (to give the X compounds in which n=2) by conventional hydroboration (boron hydride, followed by treatment with hydrogen peroxide) or by reduction of the corresponding aldehydes (for example sodium borohydride) of formula VI, for example, as indicated in Scheme II (to give the X compounds in which n=1).

The aldehydes or ketones of the formula $R^1.CHO$ or $R^1.CO.R^2$ which are new may be made, by conventional procedures well known in the art, such as are as illustrated in the accompanying Examples. The necessary Wittig reagents may be obtained by conventional procedures, for example by treating the corresponding phosphonium halides with a strong base such as sodium hydride, lithium diisopropylamide, potassium t-butoxide or butyllithium. They are generally formed in situ just prior to carrying out the condensation process (d) above.

It will be understood that the compounds of formula I wherein $R^4$ is hydroxy may also be obtained by other conventional procedures well known in the art, for example by base catalysed hydrolysis of the corresponding amides or nitriles. In addition, those compounds of formula I wherein $R^4$ is other than hydroxy may be made by conventional esterification or sulphonamidation procedures from the compounds wherein $R^4$ is hydroxy (or a reactive derivative thereof) and the appropriate alcohol, phenol or (1-4C)alkanesulphonamide. Such procedures are also within the ambit of the invention.

Whereafter, when a salt of a compound of formula I is required, it may be obtained by reaction with the appropriate base or acid affording a physiologically acceptable ion, or by any other conventional salt formation procedure.

Further, when an optically active form of a compound of formula I is required, one of the aforesaid processes may be carried out using an optically active starting material (for example as described in Examples 46 and 47). Alternatively, the racemic form of a compound of formula I may be reacted with an optically active form of a suitable organic acid or base, for example, camphorsulphonic acid, ephedrine, N,N,N-trimethyl(l-phenylethyl ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid (or base) using a conventional procedure, for example using an aqueous mineral acid such as dilute hydrochloric acid (or aqueous alkali such as aqueous sodium hydroxide).

Many of the intermediates defined herein are novel, for example those of formulae V (Ra=Rb=ethyl), VI, VII, VIII, IX and X, and are provided as further, separate features of the invention.

As stated earlier, the compounds of formula I possess significant $TXA_2$ antagonist properties and are inhibitors of $TXA_2$ synthase. The $TXA_2$ antagonism may be demonstrated in one or other of the following standard tests:

(a) The rat aortic strip metal analogous to that devised by Piper and Vane (*Nature*, 1969, 223, 29-35) using as agonist the $TXA_2$ mimetic agent known as U46619 (described by R. L. Jones et alia in "Chemistry, Biochemistry and Pharmacological Activity of Prostanoids" edited by S. M. Roberts and F. Scheinmann, at page 211; Pergamon Press, 1979);

(b) a blood platelet aggregation test based on that described by Born (*Nature*, 1962, 194, 927-929) and involving:

(i) aggregating human, citrated, platelet-rich plasma by addition of the $TXA_2$ mimetic agent U46619 so that a dose-response curve is generated;

(ii) generating a dose-response curve for U46619 stimulated platlet aggregation in the presence of increasing amounts of test compound (generally in the range $10^{-5}M$ to $10^{-10}M$); and (iii) calculating a $K_B$ value indicating potency of $TXA_2$ antagonism for the test compound, averaged over several concentrations, from the calculated 50% response value for U46619 aggregation in the presence and absence of test compound; or (c) a bronchoconstriction test involving measuring the inhibition by a test compound of the bronchoconstriction induced in Konzett-Rossler, anaesthetised guinea-pig model (as modified by Collier and James, *Brit. J. Pharmacol.*, 1967, 30, 283-307) by intravenous administration of the $TXA_2$ mimetic agent, U46619, which involves:

(i) obtaining a culmative dose-response curve to U46619 induced bronchoconstriction by intravenous administration of constant volumes of increasing concentrations of U46619 (0.2-4 µg/kg) in physiological saline solution and expressing bronchoconstriction as the maximum of that theoretically obtainable with no air flow to the test animal;

(ii) generating a culmative dose-response curve to U46619 induced bronchoconstriction at 30 minute intervals for 3 hours after oral dosing of test compound; and (iii) calculating a dose-ratio for the test compound (that is the ratio of concentration of U46619 required to cause 50% bronchoconstriction in the presence and absence of test compound) indicating the potency of $TXA_2$ antagonism.

Test (b) may conveniently be modified to demonstrate the antagonism of the effects of $TXA_2$ in vivo by assessing the effects of a test compound on the aggregation of blood platelets obtained after administration of test compound to a laboratory animal, such as a rabbit, rat, guinea pig or dog. However, when the aggregation of dog platelets is being studied it is necessary to use a predetermined, threshold concentration of the platelet aggregation agent adenosine diphosphate (about $0.4-1.2 \times 10^{-6}M$) together with the $TXA_2$ mimetic agent, U46619.

The antagonism of the effects of $TXA_2$ on the vasculature may also be demonstrated, for example in rats in the following procedure:

(d) Male rats (Alderley Park strain) are anaesthetised with sodium pentobarbital and blood pressure is monitored at the carotid artery. The $TXA_2$ mimetic agent U46619 is administered intravenously at 5 µg/kg via the jugular vein to produce 20-30 mm/Hg (2640-3970 pascal) increase in systolic blood pressure. The process is repeated twice to ensure adequacy of response. A test compound is then administered either intravenously (via the jugular vein) or orally (via a cannula) directly into the stomach and the animal challenged with U46619, five minutes after dosing with test compound and then successively every ten minutes until the hypertensive effect of U46619 is no longer blocked.

The $TXA_2$ synthase inhibitory properties of a test compound may be demonstrated using the standard in vitro procedure [test (e)] described by Howarth et alia (*Biochem. Soc. Transactions*, 1982, 10, 239-240) using a human platelet microsomal $TXA_2$ synthase preparation and using a quantitative thin layer radiochromatographic method to assess the conversion of arachidonic acid to the $TXA_2$ metabolite thromboxane $B_2$ (TXB2).

The $TXA_2$ synthase inhibitory properties of a test compound may also be demonstrated in a standard procedure involving obtaining blood samples from laboratory animals (typically rats, but also guinea pigs, rabbits or dogs) dosed with the test compound, generally by the oral route. The samples treated with anti-coagulant are first incubated at 37° C. with collagen (at about 100 micro M), then mixed with the cyclooxygenase inhibitor indomethacin (at about $10^{-3}M$), centrifuged and the level of the $TXA_2$ metabolite, $TXB_2$, determined by a standard radioimmunoassay technique. By comparison of the amount of $TXB_2$ present in the plasma from animals dosed with test compound with that in the plasma of a control group dosed with placebo, the TXA$_2$ synthase inhibitory properties may be assessed.

In general, the majority of compounds of formula I wherein R$^1$ and R$^4$ are hydroxy show effects in the following ranges in one or more of the above tests:

test (a): pA$_2$ of >5.5
test (b): K$_B$ of <1.5×10$^{-6}$M
test (c): dose ratio of >5, 1 hour after dosing at 10 mg/kg
test (d): significant inhibition of U46619 induced hypertension for at least 1 hour following oral dosing at 50 mg/kg or less
test (e): IC$_{50}$ of <1.0×10$^{-6}$M
test (f): significant inhibition of TXB$_2$ production 1 hour following a dose of 100 mg/kg or less.

No overt toxic or other untoward effects have been observed with representative compounds of formula I having effects in in vivo tests (c), (d) or (f) at several multiples of the minimum effective dose.

In general, compounds of formula I wherein R$^4$ is other than hydroxy show lower activity in the above in vitro tests but show similar activity to the compounds of formula I in which R$^4$ is hydroxy in the in vivo tests.

The compound described in Example 1 hereinafter possesses both TXA$_2$ antagonist and TXA$_2$ synthase inhibitory properties as indicated by a K$_B$ of 3.0×10$^{-7}$M in test (b) and an IC$_{50}$ of 4.0×10$^{-8}$M in test (e).

As stated previously, by virtue of their combined TXA$_2$ antagonist and TXA$_2$ synthase inhibitory properties, the compounds of formula I may be used in the therapy or prevention of diseases or adverse conditions in warm-blooded animals in which TXA$_2$ (or prostaglandins H$_2$, D$_2$ and/or F$_2$ alpha) are involved. In general, a compound of formula I will be administered for this purpose by an oral, rectal, intravenous, subcutaneous, intramuscular or inhalation route, so that a dose in the range, for example 0.01-15 mg/kg body weight, will be given up to four times per day, varying with the route of administration, the severity of the condition and the size and age of the patient under treatment.

The compounds of formula I will generally be used in the form of a pharmaceutical composition comprising a compound of formula I or, a pharmaceutically acceptable salt thereof as defined hereinabove, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example a known platelet aggregation inhibitor, hypolipidemic agent, anti-hypertensive agent, thrombolytic agent (such as streptokinase), beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition. Still further, a known TXA$_2$ antagonist, such as a preferred compound described in European patent application, Publication No. 201354, or a known TXA$_2$ synthase inhibitor such as dazoxiben or furegrelate [U63557] may be present in addition to a compound of the formula I, or a pharmaceutically acceptable salt thereof, in a composition according to the invention in order to modify the overall balance of TXA$_2$ antagonist and TXA$_2$ synthase inhibitory effects for the required therapeutic effect in any of the aforesaid diseases or disease conditions.

In addition to their use in therapeutic medicine, the compounds of formula I are also useful as pharmacological tools in the development and standardisation of test systems for the evaluation of the effects of TXA$_2$ in laboratory animals such as cats, dogs, rabbits, monkeys, rats and mice, as part of the search for new therapeutic agents. The compounds of formula I may also be used because of their TXA$_2$ antagonist and synthase inhibitory properties in helping to maintain the viability of blood and blood vessels in warm-blooded animals (or parts thereof) under-going artificial extracorporeal circulation, for example during limb or organ transplants. When used for this purpose a compound of formula I, or a physiologically acceptable salt thereof, will generally be administered so that a steady state concentration in the range, for example, 0.1 to 10 mg. per liter is achieved in the blood.

The invention will now be illustrated by the following non-limiting Examples in which Example 14 described the production of a starting material of formula V and, unless otherwise stated:

(i) concentrations and evaporations were carried out by rotary evaporation in vacuo;

(ii) operations were carried out at room temperature, that is in the range 18°-26° C.;

(iii) flash column chromatography was performed on Fluka Kieselgel 60 (catalogue no. 60738) obtained from Fluka AG, Buchs, Switzerland CH-9470;

(iv) yields are given for illustration only and are not necessarily the maximum attainable by diligent process development;

(v) proton NMR spectra were normally determined at 90 or 200 MHz in CDCl$_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; and (vi) all end-products were isolated as racemates and had satisfactory microanalyses.

EXAMPLE 1 p-Toluenesulphonic acid (0.325 g) was added to a solution of 4(Z)-6-[2,2-dimethyl-4-(3-pyridyl)-1,3-dioxan-cis-5-yl]hexenoic acid (A) (0.469 g) in acetonitrile (7 ml), and the mixture was stirred for 0.5 hours. A solution of 2-(4-methoxyphenoxy)-2-methylpropanal (0.894 g) in acetonitrile (5 ml) was added and the mixture was heated at reflux for 18 hours under an atmosphere of argon. The mixture was then allowed to cool. The solution was basified with 2M aqueous sodium hydroxide solution, and then partitioned between water and ethyl acetate. The aqueous phase was acidifed with acetic acid and extracted three times with ethyl acetate. The combined organic extracts were dried (MgSO$_4$) and concentrated to give an oil, which was purified by flash column chromatography, eluting first with dichloromethane and then methanol/dichloromethane(1:10 v/v) to give 4(Z)-6[(2,4,5-cis)-2-(1-(4-methoxyphenoxy)-1-methylethyl)-4-(3-pyridyl)-1,3-dioxan-5-yl]-hexenoic acid (0.345 g), as an oil which solidified on standing; NMR; 1.35(3H,s), 1.38(3H,s), 1.55–1.8(2H,m), 2.25–2.55(5H,m), 3.75(3H,s), 3.95–4.25(2H,m), 4.75(1H,s), 5.1–5.5(3H,m), 6.75–7.0(4H,m), 7.35–7.75(2H,m) and 8.5–8.6(2H,m).

The starting material A was prepared as follows:

(i) Methyl 2-(nicotinoyl)acetate (17.9 g, prepared by the method of E. Wenkert et al, *J. Org. Chem.*, 1983, 48, 5006) was added under argon to a solution of sodium metal (2.3 g) in methanol (200 ml) and the resulting mixture was stirred at 25° C. for 30 mins. Allyl bromide (12.0 g) was then added and stirring was continued overnight. A further amount (about 2 g) of allyl bromide was added, the mixture was stirred for 48 hours, and then concentrated. The residual oil was partitioned between water and ether and the aqueous layer was extracted three times with ether. The combined extracts were washed with saturated brine, dried (MgSO$_4$) and concentrated. The residue was purified by flash column chromatography, eluting with a mixture of petroleum ether (b.p. 60°–80°) and ethyl acetate (1:1, v/v) to give methyl 2-nicotinoyl-4-pentenoate (B) as a pale yellow oil (13.8 g); NMR 2.6–2.9(2H,m), 3.7(3H,s), 4.4(1H,m), 4.9–5.2(2H,m), 5.5–6.0(1H,m), 7.2–7.5(1H,m), 8.1–8.3(1H,m), 8.7–8.8(1H,m) and 9.1–9.2(1H,m).

(ii) A solution of B (8.8 g) in dry THF (40 ml) was added to suspension of lithium aluminum hydride (1.8 g) in dry THF (80 ml) under argon at such a rate that the temperature did not exceed 10° C. After 2 hours the mixture was cooled in ice. Ethyl acetate (20 ml) was then added to destroy excess reagent, followed by saturated aqueous ammonium chloride (50 ml). The precipitate was removed by filtration and washed with ethyl acetate. The aqueous phase was separated and extracted with ethyl acetate (3×50 ml). The combined organic fractions were washed with saturated brine, dried (MgSO$_4$) and concentrated. The residue was purified by flash column chromatography, eluting with a mixture of ethyl acetate and methanol, (95:5 v/v). to give 2-allyl-1-(3-pyridyl)-1,3-propanediol (C) (5.3 g), as an oil (mixture of diastereomers); NMR: 1.8–2.2(3H,m), 3.6–4.1(4H,m), 4.7–5.2(3H,m), 5.6–5.9(1H,m), 7.2–7.4(1H,m), 7.65–7.8(1H,m) and 8.4–8.6(2H,m).

(iii) A mixture of C (5.2 g), p-toluenesulphonic acid (5.2 g), and 2,2-dimethoxypropane (50 ml), was stirred overnight at room temperature. The pH was adjusted to 8–10 by addition of triethylamine and the solution was concentrated under reduced pressure. The residue was purified by flash column chromatography, eluting with a mixture of petroleum ether (b.p. 40°–60°) and ethyl acetate (60:40 v/v) to give 5-allyl-2,2-dimethyl-4-(3-pyridyl)-1,3-dioxane (D) (mixture of 4,5-cis and trans isomers) as an oil (4.6 g); NMR: 1.4–1.6(6H,m), 1.6–2.5 (3H,m), 3.65–4.25(2H,m), 4.5–5.7(4H,m), 7.2–7.4(1H,m), 7.6–7.8(1H,m) and 8.45–8.65(2H,m).

(iv) Ozone in oxygen was bubbled through a sodium of D (3.4 g), in ethyl acetate (130 ml) at −70° C. until a blue colour persisted throughout. Argon was then bubbled through the solution to discharge the excess ozone and a solution of triphenylphosphine (6.0 g) in ethyl acetate (50 ml) was added. The mixture was allowed to warm to room temperature and then stirred overnight. The solution was concentrated and ether (50 ml) was added to precipitate triphenylphosphine oxide. The mixture was filtered and the filtrate was concentrated to give an oil which was purified by flash column chromatography, eluting with a mixture (60:40 v/v) of ethyl acetate and petroleum ether (b.p. 40°–60°) to give initially 2,2-dimethyl-4-(3-pyridyl)-1,3-dioxan-cis-5-yl-acetaldehyde (E) as an oil (0.8 g); NMR: 1.5(3H,s), 1.55(3H,s), 2.0–2.3(1H,m), 2.3–2.5(1H,m), 2.8–3.0(1H,m), 3.8(1H,dd, J=12 Hz, 1.5 Hz), 4.3(1H,dm, J=12 Hz), 5.25(1H,d, J=3 Hz), 7.25–7.35(1H,m), 8.45–8.60(2H,m) and 9.6(1H,s); and then the corresponding 4,5-transisomer; NMR: 1.47(3H,s), 1.57(3H,s), 2.0–2.6(3H,m), 3.75–4.05(2H,m), 4.68(1H,d, J=10 Hz), 7.25–7.40(1H,m), 7.70–7.80(1H,m), 8.50–8.65(2H,m) and 9.5(1H,br s); as an oil (0.7 g).

(v) A solution of E (0.20 g) in dry tetrahydrofuran (THF) (7 ml) was added under argon to a stirred, ice-cooled solution of the ylid prepared from (3-carboxypropyl)triphenylphosphonium bromide (0.91 g) and potassium t-butoxide (0.48 g) in dry THF (30 ml). The mixture was stirred for 2 hours and then treated with ice-cooled water (50 ml). The solution was concentrated and more water was added (25 ml). The pH was adjusted to 7 by addition of a few crystals of oxalic acid and the solution was extracted with ethyl acetate (3×40 ml). The aqueous phase was then acidified to pH 4 with oxalic acid and extracted with ethyl acetate (3×50 ml). These combined extracts were washed with saturated brine (50 ml), dried (MgSO$_4$) and concentrated. The residue was purified by flash column chromatography, eluting with dichloromethane/methanol (95:5, v/v), to give 4(Z)-6-[2,2-dimethyl-4-(3-pyridyl)-1,3-dioxan-cis-5-yl]hexenoic acid (A) as an oil (0.19 g); NMR: 1.55(3H,s), 1.57(3H,s), 1.5–2.6(7H,m), 3.85(1H,dd, J=12HZ, 1.5 Hz), 4.15(1H,dm, J=12 Hz), 5.15–5.50(3H,m), 7.3–7.4(1H, m), 7.7–7.8(1H,m), 8.1(1H, br s) and 8.45–8.60(2H, m).

The 2-(4-methoxyphenoxy)-2-methylpropanal was obtained as follows:

(vi) A stirred solution of methyl magnesium iodide, [prepared from magnesium turnings, (32.8 g, 1.35M), and methyl iodide, (84.1 ml, 1.35M], in anhydrous ether, (750 ml), was treated at 0° C. under an argon atmosphere with a solution of methyl dichloroacetate, (77.18 g, 0.54M), in anhydrous ether, (50 ml), at such a rate that the temperature did not rise above 15° C. The mixture was stirred at 25° C. for 30 minutes then cooled to 0° C. Water, (100 ml), was added and the mixture was acidified to pH4 using concentrated hydrochloric acid. The layers were separated and the aqueous phase extracted with ether, (3×100 ml). The combined extracts were dried, (MgSO$_4$), and concentrated. The residual oil was distilled under reduced pressure to give 1,1-dichloro-2-hydroxy-2-methylpropane, (57.81 g), as an oil; b.p. 48°–50° C. at 20 mm Hg; NMR: 1.45(6H,s), 2.15(1H,br s) and 5.65 (1H,s).

(vii) A solution of 4-methoxyphenol, (21.72 g, 0.175 mol), in aqueous sodium hydroxide solution, (5.8M, 30 ml), was treated with cetyltrimethyl ammonium bromide, (0.255 g, 0.7 mmol), followed by a solution of 1,1-dichloro-2-hydroxy-2-methylpropane, (5.01 g, 35 mmol), in ether, (70 ml). The mixture was stirred under an argon atmosphere for 18 hours then diluted with ether, (100 ml), and extracted with aqueous sodium hydroxide solution, (2M, 4×50 ml), to remove unreacted phenol. The combined aqueous extracts were extracted with ether, (100 ml), and the organic phase was washed with aqueous sodium hydroxide solution, (2M, 50 ml), and water, (100 ml). The combined organic extracts were dried, (MgSO$_4$), concentrated and purified by flash column chromatography, eluting with ethyl acetate/hexane, (10%, v/v), to give 2-(4-methoxyphenoxy)-2-methylpropanal, (3.61 g), as an oil; NMR: 1.36(6H,s), 3.76(3H,s), 6.7–6.9(4H,m) and 9.85(1H,s).

Note: the above starting material may also be obtained using an analogous procedure to that described in European patent application, publication no. 201351 for the preparation of 2-phenoxy-2-methylpropanol.

EXAMPLE 2

Using an analogous procedure to that described in Example 1 but starting from 2-(4-t-butylphenoxy)-2-methylpropanol, there was obtained 4(Z)-6-[(2,4,5-cis)-2-(1-[4-t-butylphenoxy]-1-methylethyl)-4-(3-pyridyl)-1,3-dioxan-5-yl]hexenoic acid as an oil, which solidified on standing, in 24% yield; NMR: 1.3(9H,s,), 1.35(3H,s), 1.4(3H,s), 1.55–1.8(2H,m), 2.25–2.55(5H,m), 3.95–4.25(2H,m), 5.1–5.5(3H,m), 6.9–7.75(6H,m) and 8.5–8.6(2H,m).

The starting aldehyde was obtained as an oil in an analogous manner to that described in Example 1 from 4-t-butylphenol and 1,1-dichloro-2-hydroxy-2-methylpropane, having NMR: 1.26(9H,s), 1,41 (6H,s), 6.7–7.3(4H,m) and 9.85(1H,s).

EXAMPLE 3

5-Cyanothiophene-2-carboxaldehyde (500 mg) and p-toluene-sulphonic acid (220 mg) were added to a stirred suspension of 4(Z)-6-[2,2-dimethyl-4-(4-pyridyl)-1,3-dioxan-cis-5-yl]hexenoic acid (305 mg) in acetonitrile (10 ml). The mixture was stirred for 18 hours. Water (20 ml) and M sodium hydroxide solution (30 ml) were added and the mixture was washed with ethyl acetate (3×20 ml). The aqueous phase was acidified (acetic acid) to pH 4–5 and extracted with ethyl acetate (3×30 ml). The extracts were washed with saturated brine, dried (MgSO$_4$) and evaporated. The residual gum was crystallised from hexane/ethyl acetate to give 4(Z)-6-[(2,4,5-cis)-2-(5-cyano-2-thienyl)-4-(3-pyridyl)-1,3-dioxan-cis-5-yl]hexenoic acid (148 mg) as a colourless solid, m.p. 129°–132° C.; NMR: 1.68(1H, m), 1.84(1H, m), 2.32(4H, m), 2.54(1H, m), 4.20(2H, m), 5.05–5.95(4H, m), 5.96(1H, s), 7.17(1H, d), 7.36(1H, m), 7.53(1H, d), 7.72(1H, d) and 8.57(2H, br s); m/e 383 (M-H).

The starting 5-cyanothiophene-2-carboxaldehyde was obtained by oxidation of 5-cyano-2-methylthiophene with chromium trioxide (*Org. Synthesis, Collected Volume II*, 441, 1943) as a colourless solid (60% yield), m.p. 91°–93° C.; IR: 2210 (CN) and 1670 (CHO) cm$^{-1}$; m/e 137 (M+).

EXAMPLES 4–11

Using a similar procedure to that described in Example 3, but starting from the appropriately substituted heterocyclic aldehyde of formula R$^1$.CHO, the following acids of formula XIII were obtained in yields of 24–42%:

| Example | R$^1$ | m.p. (°C.) | Partial NMR Data |
|---|---|---|---|
| 4 | 4-Br-2-thienyl | 72–74 | 5.92(1H, s), 7.12(1H, s), 7.23(1H, m). |
| 5 | 5-Br-2-thienyl | 143–145 | 5.88(1H, s), 6.95(2H, m). |
| 6 | 4-Cl-2-thienyl | 112–116 | 5.91(1H, s), 7.10(2H, m) |
| 7 | 2-thienyl | 149–151 | 5.97(1H, s), 7.02(1H, m), 7.18(1H, m). |
| 8 | 5-Cl-2-thienyl | 153–155 | 5.85(1H, s), 6.80(1H, d), 6.93(1H, d). |
| 9 | 2-furyl | 139–141 | 5.80(1H, s), 6.38(1H, m), 6.53(1H, m), 7.53(1H, m). |
| 10 | 5-Br-2-furyl | 157–158 | 5.75(1H, s), 6.33(1H, d), 6.55(1H, d). |
| 11 | 3-thienyl | 146–148 | 5.80(1H, s), 7.30(3H, m). |

Note: The starting aldehydes of formula R$^1$.CHO were commercially available but may be obtained by standard procedures such analogous to those described herein.

EXAMPLE 12

2M Sodium hydroxide solution (2.0 ml) was added to a stirred solution of methyl 4(Z)-6-[2,2-bis(trifluoromethyl)-4-(3-pyridyl)-1,3-dioxan-cis-5-yl]hexenoate (G) (420 mg) in methanol (10 ml). After 2 hours, water (40 ml) was added. The solution was acidified with acetic acid and then extracted with ethyl acetate (4×20 ml). The combined extracts were washed with saturated brine (20 ml), and then dried (MgSO$_4$). The solvent was removed by evaporation to give an oil which was purified by flash chromatography, eluting with ethyl acetate/hexane/acetic acid (70:30:0.1 by volume), to give a white solid. This was recrystallised from ethyl acetate/hexane to give crystalline 4(Z)-6-[2,2-bis(trifluoromethyl)-4-(3-pyridyl)-1,3-dioxan-cis-5-yl]hexenoic acid (246 mg), m.p. 119°–120° C.; NMR: 1.67(1H, m), 1.94(1H, m), 2.29(4H, m), 2.51(1H, m), 4.22(1H, d, J=11 Hz), 4.45(1H, dm, J=11 Hz), 5.20(1H, m), 5.50(1H, m), 5.62(1H, d, J=1.5 Hz), 7.40(1H, m), 7.74 (1H, dm, J=7 Hz) and 8.60(2H, m); microanalysis, found: C,49.4; H,4.2; N, 3.2%; C$_{17}$H$_{17}$NO$_4$F$_6$ requires: C,49.4; H,4.2; N, 3.4%; m/e 414 (M+H)$^+$.

The necessary starting material G was prepared as follows:

(i) 1M Hydrochloric acid (10 ml) was added to a solution of 4(Z)-6-[2,2-dimethyl-4-(3-pyridyl)-1,3-dioxan-cis-5-yl]hexenoic acid (1.42 g) in tetrahydrofuran (THF) (15 ml) and the mixture was stirred for 2 hours. Water (40 ml) was added and the pH adjusted to 12 with 2M sodium hydroxide solution. The mixture was washed with ethyl acetate (2×25 ml), acidified to pH 5 with acetic acid, and then saturated with solid sodium chloride. The aqueous mixture was then extracted with ethyl acetate (12×50 ml) and the combined extracts were dried (MgSO$_4$). The solvent was removed by evaporation to give 4(Z)-erythro-8-hydroxy-7-hydroxymethyl-8-(3-pyridyl)-4-octenoic acid (H) as a brown oil (1.114 g), which was used without further purification. For the purposes of characterisation, a sample was purified by flash chromatography eluting with methanol/dichloromethane (1:5 v/v); NMR: 1.91(3H, m), 2.23(5H, m), 3.59(2H, m), 5.02(1H, m), 5.35(3H, m), 7.30(1H, m), 7.76(1H, m), 8.46(1H, dd, J=4 and 1 Hz) and 8.60(1H, d, J=2 Hz).

(ii) p-Toluenesulphonic acid monohydrate (1.06 g) was added to a solution of H (1.114 g) in methanol (25 ml) and the mixture was stirred for 3 hours. Triethylamine (0.83 ml) was added and the mixture was concentrated to a small volume. Saturated brine (20 ml) was added and the mixture was extracted with ethyl acetate (4×25 ml). The combined organic extracts were washed with saturated brine (10 ml), dried (MgSO$_4$) and the solvent was removed by evaporation. The resultant oil was purified by MPLC, eluting with methanol/dichloromethane (1:12 v/v) to give methyl 4(Z)-erytrho-8-hydroxy-7-hydroxymethyl-8-(3-pyridyl)-4-octenoate (I) as an oil (1.044 g); NMR (250 MHz, CDCl$_3$): 1.82(2H, m), 2.16(1H, m), 2.44(4H, m), 2.91(2H, b), 3.67(3H, s), 3.81(2H, d, J=3 Hz), 5.20(1H, d, J=2 Hz), 5.30(2H, m), 7.33(1H, m), 7.79(1H, m), 8.51(1H, m) and 8.61(1H, m).

(iii) A solution of methanesulphonyl chloride (0.32 ml) in dichloromethane (2.0 ml) was added during ten minutes to a stirred solution of I (995 mg) and triethylamine (0.59 ml) in dichloromethane (20 ml). The mixture was stirred for a further 1 hour and then diluted with ethyl acetate (50 ml). The subsequent mixture was washed with water (2×15 ml), saturated brine (15 ml), and dried (MgSO$_4$).

The solvent was removed by evaporation to give an oil which was purified by MPLC, eluting with methanol/dichloromethane (1:32 v/v), to give methyl 4(Z)-erythro-8-hydroxy-7-(methylsulphonyloxymethyl)-8-(3-pyridyl)-4-octenoate (J) as a colourless oil (886 mg); NMR (250 MHz, CDCl$_3$): 2.24(8H, m), 3.01(3H, s), 3.68(3H, s), 4.10(1H, m), 4.31(1H, m), 5.02(1H, d, J=2H), 5.38(2H, m), 7.34(1H, m), 7.77(1H, d J=7 Hz) and 8.57(2H, m).

(iv) Anhydrous potassium carbonate (2.78 g) and hexafluoroacetone sesquihydrate (4.53 g) were added to a solution of J (500 mg) in dry THF (10 ml). The mixture was stirred for 18 hours at 60° C., cooled, and water (50 ml) added. The resulting solution was extracted with ether (4×20 ml), and the combined organic extracts were washed with saturated brine (20 ml), then dried (MgSO$_4$). The solvent was removed by evaporation and the resultant residue purified by flash chromatography, eluting with ethyl acetate/hexane (40:60 v/v), to give methyl 4(Z)-6-[2,2-bis(trifluoromethyl)-4-(3-pyridyl)-1,3-dioxan-cis-5-yl]hexenoate (G) as a pale yellow oil (425 mg): NMR: 1.61(1H, m), 1.91(1H, m), 2.27(4H, m), 2.54(1H, m), 3.65(3H, s), 4.23(1H, bd, J=11 Hz), 4.44(1H, dm, J=11 Hz) 5.16(1H, m), 5.46(1H, m), 5.62(1H, d, J=1.5 Hz), 7.38(1H, m), 7.70(1H, dm, J=7 Hz) and 8.58(2H, m); m/e 428 (M+H)$^+$.

EXAMPLE 13

An analogous hydrolysis procedure was used to that described in Example 12, but starting from methyl 4(Z)-6-[(2,4,5-cis)-2-pentafluoroethyl-4-(3-pyridyl)-1,3-dioxan-5-yl]hexenoate. Evaporation of the extracts of the acidified reaction mixture gave a colourless oil which oil solidified on trituration with hexane. Recrystallisation of the solid from ethyl acetate/hexane gave 4(Z)-6-[(2,4,5-cis)-2-pentafluoroethyl-4-(3-pyridyl)-1,3-dioxan-5-yl]hexenoic acid (61%); m.p. 121°-124° C.; NMR (250 MHz, CDCl$_3$): 1.68(1H, m), 1.85(1H, m), 2.30(4H, m), 2.51(1H, m), 4.03(1H, d, J=11 Hz), 4.31(1H, d, J=11 Hz), 5.21(3H, m), 5.46(1H, m), 6.35(1H, b), 7.39(1H, m), 7.72(1H, m) and 8.58 (2H, bs); microanalysis, found: C,51.4; H,4.5; N,3.3%; C$_{17}$H$_{18}$NO$_4$F$_5$ requires; C,51.6; H.4.6; N,3.5%; m/e 396 (M+H)$^+$.

The starting methyl ester was prepared in a similar manner to that in Example 12 (iv) but using pentafluoropropionaldehyde instead of hexafluoroacetone sesquiihydrate. Methyl 4(Z)-6-[(2,4,5-cis)-2-pentafluoroethyl-4-(3-pyridyl)-1,3-dioxan-5-yl]hexenoate as a yellow oil (59%); NMR: 1.61(1H, m), 1.81(1H, m), 2.30(4H, m), 2.53(1H, m), 3.66(3H, s), 4.02(1H, dm, J=11 Hz), 4.29(1H, dd, J=11,1.5 Hz), 5.21(3H, m), 5.45(1H, m), 7.34(1H, m), 7.68(1H, dm, J=7 Hz) and 8.56(2H, m); m/e 410 (M+H)$^+$.

EXAMPLE 14

2M sodium hydroxide solution (3.0 ml) was added to a stirred solution of methyl 4(Z)-6-[2,2diethyl-4-(3-pyridyl)-1,3-dioxan-cis-5-yl]hexenoate (218 mg) in methanol (10 ml). After 5 hours water (20 ml) was added, the solution acidified with acetic acid, and extracted with ethyl acetate (3×15 ml). The combined organic extracts were washed with saturated brine (10 ml), and then dried (MgSO$_4$). The solvent was removed by evaporation to give an oil which was purified by flash chromatography, eluting with ethyl acetate/hexane/acetic acid (70:30:0.1 by volume) to give 4(Z)-6-[2,2-diethyl-4-(3-pyridyl)-1,3-dioxan-cis-5-yl]hexenoic acid as a pale yellow oil (145 mg); NMR: 0.86(3H, t, J=7 Hz), 1.08(3H, t, J=7 Hz), 1.66(4H, m), 1.95(2H, m), 2.30(4H, m), 2.52(1H, m), 3.84(1H, d, J=11 Hz), 4.15 (1H, d, J=11 Hz), 5.23(2H, m), 5.40(1H, m), 6.32(1H, br), 7.35(1H, m), 7.75(1H, dm, J=7 Hz) and 8.55(2H, m); m/e 334 (M+H)$^+$. On keeping for several weeks at 4° C., the oil slowly crystallised. Trituration of the solid with hexane gave crystalline material of m.p. 72°-77° C.; microanalysis, found: C,68.2; H,8.4; N,4.2%; C$_{19}$H$_{27}$O$_4$ requires: C,68.4; H,8.2; N, 4.26%

The necessary starting methyl ester was prepared as follows:

(i) A solution of 4(Z)-6-[2,2-diethyl-4-(3-pyridyl)-1,3-dioxan-cis-5-yl]hexenoic acid (5.0 g) in methanol (50 ml) was treated with p-toluenesulphonic acid monohydrate (3.74 g). The mixture was stirred for 4 hours and then added to 5% w/v sodium hydrogen carbonate solution (75 ml). This mixture was acidified (acetic acid) and extracted with ethyl acetate (4×20 ml). The combined extracts were washed with water (10 ml), then dried (MgSO$_4$) and the solvent removed by evaporation. The residual oil was purified by flash chromatography, eluting with dichloromethane/methanol (92:8 v/v) to give methyl 4(Z)-Z-erythro-8-hydroxy-7-hydroxymethyl-8-(3-pyridyl)-4 -octenoate as an oil (4.20 g) with an NMR spectrum which was closely similar to that for the diol obtained in Example 12(ii).

(ii) A solution of the diol from (i) (400 mg), p-toluene sulphonic acid monohydrate (293 mg), diethylketone (290 microliters) and trimethylorthoformate (383 microliters) in acetonitrile (10 ml) was stirred for 4 hours. 5% w/v Sodium hydrogen carbonate solution (20 ml) was added and the mixture extracted with ethyl acetate (3×25 ml). The combined extracts were washed with saturated brine (15 ml), and then dried (MgSO$_4$). The solvent was removed by evaporation and the residual oil purified by flash chromatography, eluting with ethyl acetate/hexane (55:45 v/v) to give methyl 4(Z)-6-[2,2-diethyl-4-(3-pyridyl)-1,3-dioxane-cis-5-yl]hexenoate as a pale yellow oil (218 mg); NMR (250 MHz, CDCl$_3$): 0.87 (3H, t, J=7 Hz), 1.08 (3H, t, J=7 Hz), 1.49(1H, m), 1.61(1H, m), 1.75(2H, m), 1.97(2H, m), 2.30(4H, m), 2.55(1H, m), 3.65(3H, s), 3.81(1H, d, J=11 Hz), 4.13(1H, d, J=11 Hz), 5.20(1H, m), 5.28(1H, d, J=2 Hz), 5.38(1H, m), 7.31(1H, m), 7.70(1H, d, J=7 Hz) and 8.54(2H, m); m/e 348 (M+H)+.

EXAMPLE 15

In a similar manner to Example 14 but starting from methyl 4(Z)-6-[2,2-diisopropyl-4-(3-pyridyl)-1,3-dioxan-cis-5-yl]hexenoate, there was obtained 4(Z)-6-[2,2-diisopropyl-4-(3-pyridyl)-1,3-dioxan-cis-5-yl]hexenoic acid as a pale yellow oil in 82% yield; NMR: 1.04(12H, m), 1.59(2H, m), 2.13(1H, m), 2.28(4H, m), 2.50(1H, m), 2.96(1H, m), 3.82(1H, d, J=11 Hz), 4.18(1H, d, J=11 Hz), 5.25(2H, m), 5.42(1H, m), 7.33(1H, m), 7.74(1H, dm, J=7 Hz) and 8.64(2H, m); m/e 362 (M+H)+. On keeping at 4° C. for several weeks, this oil slowly crystallised. Trituration of the solid with hexane gave crystalline material of m.p. 74°-82° C.; microanalysis, found C, 69.1; H, 8.8; N, 3.9%; $C_{21}H_{31}NO_4.0.25H_2O$ requires: C, 68.9; H, 8.6; N, 3.8%.

The starting ester was prepared using a similar procedure to that in Example 14(ii) except that 2,4-dimethyl-3-pentanone was used in place of diethylketone. Thus, methyl 4(Z)-6-[2,2-diisopropyl-4-(3-pyridyl)-1,3-dioxan-cis-5-yl]hexenoate was obtained as a pale yellow oil(44%); NMR (250 MHz, CDCl$_3$): 1.07(12H, m), 1.57(2H, m), 2.13(1H, m), 2.30(4H, m), 2.53(1H, m), 2.96(1H, m), 3.64(3H, s), 3.80 (1H, dd, J=11, 1.5 Hz), 4.14(1H, dm, J=11 Hz), 5.20(1H, m), 5.28(1H, d, J-1.5 Hz), 5.35(1H, m), 7.30(1H, m), 7.20(1H, d, J=7 Hz) and 8.55(2H, m); m/e 376 (M+H)+.

EXAMPLE 16

Using a similar procedure to that described in Example 1, but using 2-methyl-2-(4-methylsulphonylphenoxy)propanal as the aldehyde, there was obtained 4-(Z)-6-[(2,4,5-cis)-2-(1-methyl-1-(4-methylsulphonylphenoxy)ethyl)-4-(3-pyridyl)-1,3-dioxan-5-yl]hexenoic acid as an oil in 20% yield; NMR: 1.45(6H,s), 1.8-2.45(7H,m), 3.2(3H,s), 3.95-4.1 (2H, m), 4.9(1H,s), 5.15-5.45(3H, m), 7.2-7.85(6H, m), 8.45-8.5(2H,m).

The necessary aldehyde was obtained by an analogous procedure to that described in connection with Example 19 starting from 4-(methylthio)phenol which was converted to ethyl 2-methyl-2-(4-(methylthio)-phenoxy)propionate [oil, 20% yield; NMR: 1.25(3H,t J=7 Hz), 1.6(6H,s), 2.45(3H,s), 4.25(2H,q J=7 Hz), 6.75-7.2(4H,m)]. This ester was oxidised with m-chloroperbenzoic acid in dichloromethane at ambient temperature to give, after conventional work-up, ethyl 2-methyl-2-(4-methylsulphonylphenoxy)propionate [oil, slowly solidifying: 92% yield; NMR: 1.25(3H,q J=7 Hz), 1.65(6H,s), 3.0(3H,s), 4.25(2H,q J=7 Hz), 6.9-6.95(2H,m), 7.8-7.85(2H,m)] which was then reduced with DIBAL to give 2-methyl-2-(4-methylsulphonylphenoxy)propanal as a solid (66% yield); NMR: 1.5(6H,s), 3.05(3H,s), 6.9-7.0(2H,m), 7.8-7.9(2H,m), 9.8(1H,s).

EXAMPLES 17-19

Using an analogous procedure to that described in Example 1 but using the appropriate aldehyde, there were obtained: (Example 17): 4(Z)-6-[(2,4,5-cis)-2-[2-methoxyphenoxy]-1-methylethyl]-4-(3-pyridyl)-1,3-dioxan-5-yl]hexenoic acid as an oil, which solidified on keeping, to give solid in 40% yield; NMR: 1.35(3H, s), 1.40(3H,s), 1.55-1.80(2H, m), 2.20-2.55(5H, m), 3.78(3H, s), 3.95-4.25(2H, m), 4.80(1H,s), 5.10-5.50(4H, m), 6.80-7.10(4H, m), 7.40-7.75(2H, m) and 8.45-8.60(2H, m), starting from 2-methyl-2-(2-methoxyphenoxy)propanal;

(Example 18): 4(Z)-6-[(2,4,5-cis)-2-(1-[2-methylphenoxy]-1-methylethyl)-4-(3-pyridyl)-1,3-dioxane-5-yl]hexenoic acid as an oil, which solidified on keeping, to give solid in 15% yield; NMR: 1.40(3H,s), 1.45(3H,s), 1.50-1.80(2H, m), 2.25(3H, s), 2.15-2.60(5H, m), 3.95-4.25)2H, m), 4.85(1H, s), 5.10-5.50(4H, m), 6.90-7.15(4H, m), 7.30-7.75(2H, m), 8.50-8.60(2H, m), starting from 2-methyl-2-(2-methylphenoxy)propanal; and (Example 19): 4(Z)-6-[(2,4,5-cis)-2-(1-[2-nitro-4-methylphenoxy]-1-methylethyl)-4-(3-pyridyl)-1,3-dioxane-5-yl]hexenoic acid as an oil, which solidified on keeping, to give in 28% yield; NMR: 1.45(6H, s), 1.50-1.80(2H, m), 2.35(3H, s), 2.15-2.50(5H, m), 3.90-4.20(2H, m), 4.80(1H, s), 5.05-5.50(3H,m), 7.10-7.70(5H, m) and 8.45-8.60(2H, m). starting from 2-methyl-2-(2-nitro-4-methylphenoxy)propanal.

The necessary starting aldehydes were obtained as follows:

(17) 2-methyl-2-(2-methoxyphenoxy)propanal: obtained as an oil, NMR: 1.35(6H, s), 3.75(3H, s) and 6.80-7.25(4H, m), using a procedure analogous to that described in Example 1 but starting from 2-methoxyphenol and 1,1-dichloro-2-hydroxy-2-methylpropane;

(18) 2-methyl-2-(2-methylphenoxy)propanal: obtained as an oil, NMR: 1.45(6H, s), 2.25(3H, s) and 6.60-7.20(4H, m), using a procedure analogous to that described in Example 1 but starting from 2-methylphenol and 1,1-dichloro-2-hydroxy-2-methylpropane; and

(19) 2-methyl-2-(2-nitro-4-methylphenoxy)propanal:
(i) A solution of 2-nitro-4-methylphenol (11.48 g) in 1,3-dimethyl-3,4,5,6-tetrahydro-2(1H)-pyrimidinone (DMPU) (50 ml) was cooled at 5° C. and treated with portions of sodium hydride (55% w/w dispersion in mineral oil, 3.27 g). The mixture was stirred at room temperature for 2 hours, then cooled to 5° C. and treated with ethyl 2-bromo-2-methylpropionate (13.15 g). The mixture was heated at about 100° C. for 18 hours, then cooled to room temperature and poured into a mixture of aqueous sodium hydroxide solution (1M) and ethyl acetate. The organic solution was separated and washed twice with 1M sodium hydroxide solution, then dried (MgSO$_4$) and concentrated. The resulting oil was purified by flash column chromatography, eluting with a mixture of ethyl acetate and hexane, (increasing from 5:95 v/v to 10:90 v/v), to give ethyl 2-methyl-2-(2-nitro-4-methylphenoxy)propionate (4.48 g) as an oil; NMR: 1.25 (3H, t), 1.60(6H, s), 2.35(3H, s), 4.25(2H, q) and 6.8-7.6(3H, m).

(ii) A solution of ethyl 2-methyl-2-(2-nitro-4-methylphenoxy)propionate (4.47 g) in toluene (50 ml) was cooled to −78° C. and treated dropwise with diisobutylaluminium hydride (DIBAL, 11.3 ml, 1.5M solution in toluene). The mixture was stirred for 2 hours and then additional DIBAL was added until reaction was complete, (ca. 4.4 ml) as monitored by thin layer chromatographic (tlc). The reaction was quenched by addition of aqueous ammonium chloride solution and ether. The resulting mixture was clarified by filtration through kieselguhr. The organic phase was separated, dried (MgSO$_4$) and concentrated to give an oil. Purification by flash column chromatography, eluting with a mixture of ethyl acetate and hexane (increasing from 10:90 v/v to 15:85 v/v), gave 2-methyl-2-(2-nitro-4- methylphenoxy)propanal as an oil, (1.89 g); NMR: 1.45(6H, s), 2.35(3H, s), 6.8–7.6(3H, m) and 9.85(1H, s).

EXAMPLE 20

A solution of 4(Z)-6-[(2,4,5-cis)-2-(1-[2-methoxyphenoxy]-1-methylethyl)-4-(3-pyridyl)-1,3-dioxan-5-yl]hexenoic acid (0.331 g) in DMPU (6 ml) maintained at 5° C. was treated sequentially with sodium hydride (216 mg, 50% w/w dispersion in mineral oil) and ethanethiol (0.3 ml) and the mixture was then heated at 130°–135° C. for 3 hours. The mixture was cooled to room temperature and poured into a mixture of ethyl acetate and 1M aqueous sodium hydroxide solution. The organic phase was separated and extracted twice with sodium hydroxide solution. The combined aqueous extracts were then washed with dichloromethane and acidified to pH5–6 using acetic acid. The mixture was extracted three times with dichloromethane and these combined extracts were dried (MgSO4) and concentrated to give an oil. Purification by flash column chromatography, eluting with a mixture of methanol and dichloromethane (3:97 to 10:90, v/v) gave 4(Z)-6-[(2,4,5-cis)-2-(1-[2-hydroxyphenoxy]-1-methylethyl)-4-(3-pyridyl)-1,3-dioxan-5-yl]hexenoic acid as an oil which solidified on keeping to give solid (0.253 g); NMR: 1.35(3H, s), 1.45(3H, s), 1.55–1.80(2H, m), 2.20–2.55(5H, m), 4.00–4.34(2H, m), 4.80(1H, s), 5.15–5.55(3H, m), 6.70–7.05(4H, m), 7.40–7.75(2H, m) and 8.50–8.65(2H, m).

EXAMPLE 21

Using an analogous procedure to that described in Example 1 but using 2-methoxycinnamaldehyde as the aldehyde component, there was obtained 4(Z)-6-[(2,4,5-cis)-2-(2E-[2-methoxyphenyl]ethenyl)-4-(3-pyridyl)-1,3-dioxan-5-yl]hexenoic acid as an oil, which solidified on keeping to give solid in 18% yield; NMR: 1.60–1.80(2H, m), 2.15–2.65(5H, m), 3.85(3H, s), 4.00–4.30(2H, m), 5.10–5.50(4H, m), 6.30–6.40(1H, m), 6.85–7.85(7H, m) and 8.50–8.65(2H, m).

EXAMPLE 22

The acid catalysed aldehyde/ketone exchange reactions described in any of the preceding Examples may also be performed using 4(Z)-6-[2,2-diethyl-4-(3-pyridyl)-1,3-dioxan-cis-5-yl]hexenoic acid (described in Example 14) instead of the 2,2-dimethyl derivative [compound (A) described in part (v) of Example 1]. In general largely similar yields of compounds of the formula I may be obtained.

EXAMPLE 23

2-Naphthaldehyde (0.468 g) and p-toluenesulphonic acid (0.22 g) were added to a solution of 4(Z)-6-[2,2-dimethyl-4-(3-pyridyl)-1,3-dioxan-cis-5-yl]hexenoic acid (A, as described in Example 1) (0.305 g) in acetonitrile (10 ml), under an atmosphere of argon. The mixture was heated at reflux for 18 hours and then allowed to cool. Ethyl acetate (10 ml) was added and the mixture was extracted with 2M aqueous sodium hydroxide solution (60 ml). The basic extract was acidified to pH4 with acetic acid and extracted with ethyl acetate (90 ml). The combined organic extracts were dried (MgSO4) and concentrated to give an oil, which was purified by flash column chromatography, eluting with methanol/dichloromethane (1:10 to 1:5 v/v), to give 4(Z)-6-[(2,4,5-cis)-2-(2-naphthyl)-4-(3-pyridyl)-1,3-dioxan-cis-5-yl]-hexenoic acid, as a solid, (0.224 g), m.p. 138°–142° C.; NMR: 1.74 (2H,m), 2.28 (4H,m), 2.64 (1H,m), 4.18–4.34(2H,m), 5.27 (3H,m), 5.43 (1H,m), 5.88 (1H,s), 7.33–7.68 (4H,m), 7.85–8.02 (5H,m) and 8.52–8.63 (2H,m); m/e 404 (M+H)+; microanalysis, found: C, 73.5; H, 6.3; N, 3.3%; $C_{25}H_{25}NO_4$, $0.25H_2O$ requires: C, 73.6; H, 6.3; N, 3.4%.

EXAMPLE 24

Using an analogous procedure to that described in Example 23 but starting from 3-benzyloxybenzaldehyde, there was obtained 4(Z)-6-[(2,4,5-cis)-2-(3-benzyloxyphenyl)-4-(3-pyridyl)-1,3-dioxan-cis-5-yl]hexenoic acid, as a colourless solid, m.p. 125°–128° C., in 43% yield; NMR: 1.75 (2H,m), 2.28 (4H,m), 2.55 (1H,m), 4.12–4.28 (2H,m), 4.85 (1H,m), 5.12 (2H,s), 5.27 (2H,m), 6.98–7.75 (11H,m) and 8.58 (2H,m); m/e 459 (M+H)+; microanalysis, found: C, 72.8; H, 6.4; N, 2.9% $C_{28}H_{29}NO_5$ requires: C, 73.2; H, 6.4; N, 3.0%.

EXAMPLES 25–45

Using an analogous procedure to that described in Example 1, but starting from the appropriate aldehyde of the formula $R^1$.CHO and dioxane hexenoic acid A the following compounds of the formula XIII were obtained:

(Example 25): $R^1$=3-(4-cyanobenzyloxy)phenyl; isolated as a solid, m.p. 149°–150° C.; partial NMR: 5.70(1H, s), 6.95(1H,m), 7.28(4H,m), 7.55(2H,d), 7.65(2H,d), 7.73(1H,d), 8.53(1H,m), 8.62(1H,s);

(Example 26): $R^1$=1-naphthyl; isolated as a solid, m.p. 171°–172° C.; partial NMR: 6.3(1H,s), 7.32(1H,m), 7.52(3H,m), 7.85(4H,m), 8.22(1H,s), 8.52(1l,d), 8.63(1H,s);

(Example 27): $R^1$=4-(4-cyanobenzyloxy)phenyl; isolated as a solid, m.p. 162°–164° C.; partial NMR; 5.69(1H,s), 6.97(2H,d), 7.36(1H,m), 7.52(4H,m), 7.70(3H,m), 8.53(2H,m);

(Example 28): $R^1$=2-benzyloxyphenyl; isolated as a solid, m.p. 142°–144° C.; partial NMR: 6.15(1H,s), 6.93(1H,d), 7.05(1H,t), 7.31(7H,m), 7.78(2H,s), 8.51(1H,d), 8.58(1H,s);

(Example 29): $R^1$=4-benzyloxyphenyl; isolated as a solid, m.p. 200°–204° C.; partial NMR: 5.72(1H,s), 7.02(2H,d), 7.18(1H,m), 7.40(7H,m), 7.72(1H,s), 8.48(1H,d), 8.53(1H,s);

(Example 30): $R^1$=4-(3-pyridylmethoxy)phenyl; isolated as a solid, m.p. 174°–177° C.; partial NMR: 5.62(1H,s), 6.93(2H,d), 7.25(2H,d), 7.43(2H,d), 7.69(2H,s), 8.50(4H,m);

(Example 31): $R^1$=4-phenoxyphenyl; isolated as a solid, m.p. 142°–144° C.; partial NMR: 5.72(1H,s), 7.07(5H,s), 7.35(3H,s), 7.55(2H,s), 7.78(1H,m), 8.57(2H,m);

(Example 32): $R^1$=3-phenoxyphenyl; isolated as a solid, m.p. 130°–132° C.; partial NMR: 5.72(1H,s), 7.07(4H,m), 7.35(6H,s), 7.82(1H,m), 8.55(2H,m);

(Example 33): $R^1$=3-(3-pyridylmethoxy)phenyl; isolated as a solid, m.p. 104°–105° C.; 5.70(1H,s), 6.98(1H,m), 7.18(1H,m), 7.33(4H,m), 7.71(1H,m), 7.88(1H,m), 8.55(3H,m), 8.82(1H,m);

(Example 34): $R^1$=2-(4-cyanobenzyloxy)phenyl; isolated as a solid, m.p. 159°–162° C.; partial NMR: 6.15(1H,s), 6.88(1H,d), 7.09(1H,t), 7.37(2H,m), 7.47(2H,d), 7.58(2H,d), 7.77(2H,m), 8.55(2H,m);

(Example 35): $R^1$=2-(3-pyridylmethoxy)phenyl; isolated as a solid, m.p. 131°–135° C.; partial NMR: 6.15(1H,s), 6.92(1H,d), 7.08(1H,t), 7.30(3H,m), 7.72(3H,m), 8.60(4H,m);

(Example 36): $R^1$=4-benzyloxy-3-nitrophenyl; isolated as a solid, m.p. 150°-152° C.; partial NMR: 5.70(1H,s), 7.12(1H,d), 7.38(6H,s), 7.73(2H,m), 8.04(1H,d), 8.57(2H,d);

(Example 37): $R^1$=3-(1-naphthylmethoxy)phenyl; isolated as a solid, m.p. 115°-117° C.; partial NMR: 5.70(1H,s), 6.52(1H,m), 7.03(1H,m), 7.18(1H,d), 7.33(3H,m), 7.47(3H,m), 7.60(1H,d), 7.81(3H,m), 8.05(1H,m), 8.55(2H,m);

(Example 38): $R^1$=3-(2,5-dimethoxybenzyloxy)phenyl; isolated as a solid, m.p. 53°-54° C.; partial NMR: 5.72(1H,s), 6.82(2H,m), 7.00(1H,m), 7.15(2H,m), 7.31(4H,m), 7.82(1H,m), 8.57(2H,m);

(Example 39): $R^1$=2-(4-pyridylmethoxy)phenyl; isolated as a solid, m.p. 115°-117° C.; partial NMR: 6.14(1H,s), 6.87(1H,d), 7.0(1H,t). 7.12(1H,m), 7.60(7H,m), 8.6(2H,m).

(Example 40): $R^1$=2-chloro-1-naphthyl; isolated as a solid, m.p. 188°-190° C.; partial NMR: 6.73(1H,s), 7.2(1H,s), 7.46(2H,m), 7.62(1H,m), 7.75(3H,m), 8.53(2H,m), 9.02(1H,d);

(Example 41): $R^1$=2-(2-pyridylmethoxy)phenyl; isolated as a solid, m.p. 86°-88° C.; partial NMR: 6.18(1H,s), 6.92(1H,d), 7.05(1H,t), 7.18(1H,t), 7.29(2H,m), 7.45(1H,d), 7.57(1H,d), 7.76(2H,dd), 8.55(3H,m);

(Example 42): $R^1$=2-(4-nitrobenzyloxy)phenyl; isolated as a solid, m.p. 166°-168° C.; partial NMR: 6.14(1H,s), 6.88(1H,d), 7.11(1H,t), 7.32(2H,m), 7.50(2H,d), 7.76(2H,m), 8.16(2H,m), 8.59(2H,m);

(Example 43): $R^1$=3-benzyloxy-4-methoxyphenyl; isolated as a solid, m.p. 128°-130° C.; partial NMR: 5.62(1H,s), 6.90(1H,d), 7.12(2H,m), 7.44(6H,m), 7.68(1H,m), 8.55(2H,m);

(Example 44): $R^1$=3-(3-cyanobenzyloxy)-4-methoxyphenyl; isolated as a solid, m.p. 148°-149° C.; partial NMR: 5.63(1H,s), 6.92(1H,d), 7.13(2H,m), 7.32(1H,m), 7.45(1H,m), 7.58(1H,m), 7.68(2H,m), 7.80(1H,s), 8.55(2H,m);

(Example 45): $R^1$=4-benzyloxy-3-cyanophenyl, isolated as a solid, m.p. 164°-165° C.; partial NMR: 7.41(7H,m), 7.78(3H,m), 8.48(1H,dd), 8.55(1H,d).

The novel starting benzaldehydes of formula $R^1$.CHO were obtained by essentially the same general procedure, starting from the appropriate hydroxybenzaldehyde and appropriate benzyl bromide or (bromomethyl)pyridine. These starting materials were heated together in the presence of an excess of anhydrous potassium carbonate in ethyl methyl ketone under reflux for 2-18 hours until the reaction was essentially complete as judged by thin layer chromatographic analysis (TLC) on silica. The product was then isolated by concentration of the supernatant reaction mixture and flash chromatographic purification of the residual material using hexane/ethyl acetate (up to 30% v/v) as eluant. The resultant benzaldehydes of formula $R^1$.CHO were used as soon as possible and had the following properties:

(1) 3-(4-cyanobenzyloxy)benzaldehyde; m.p. 96°-97° C.; partial NMR: 5.18(2H,s), 7.24(1H,m), 7.50(5H,m), 7.68(2H,d), 9.98(1H,s).

(2) 4-(4-cyanobenzyloxy)benzaldehyde; m.p. 105°-106° C.; partial NMR: 5.23(2H,s), 7.06(2H,d), 7.54(2H,d), 7.69(2H,d), 7.86(2H,d), 9.90(1H,s).

(3) 2-benzyloxybenzaldehyde; m.p. 42°-44° C.; partial NMR: 5.20(2H,s), 7.03(2H,s), 7.44(6H,m), 7.86(1H,m), 10.58(1H,s).

(4) 4-(3-pyridylmethoxy)benzaldehyde; m.p. 75°-77° C.; partial NMR: 5.16(2H,s), 7.02(2H,m), 7.30(1H,m), 7.76(3H,m), 8.63(2H,m), 9.95(1H,s).

(5) 3-(3-pyridylmethoxy)benzaldehyde; m.p. 48°-50° C.; partial NMR: 5.09(2H,s), 7.47(4H,m), 7.70(1H,m), 8.47(2H,m), 9.90(1H,s).

(6) 2-(4-cyanobenzyloxy)benzaldehyde; m.p. 102-103; partial NMR: 5.28(2H,s), 7.01(2H,m), 7.55(3H,m), 7.70(2H,m), 7.88(1H,m), 10.55(1H,s).

(7) 2-(3-pyridylmethoxy)benzaldehyde; m.p. 58°-59° C.

(8) 4-benzyloxy-3-nitrobenzaldehyde; m.p. 86°-88° C.; partial NMR: 5.34-(2H,s), 7.24(2H,m), 7.42(4H,m), 8.03(1H,dd), 8.37(1H,d), 9.93(1H,s).

(9) 3-(1-naphthylmethoxy)benzaldehyde; m.p. 63°-64° C.; partial NMR: 5.55(2H,s), 7.27(1H,m), 7.52(7H,m), 7.87(2H,m), 8.03(1H,m), 9.98(1H,S).

(10) 3-(2,5-dimethoxybenzyloxy)benzaldehyde; obtained as an oil; partial NMR: 5.28(2H,s), 6.83(2H,d), 7.05(1H,m), 7.26(1H,m), 7.45(3H,m), 9.97(1H,s).

(11) 2(4-pyridylmethoxy)benzaldehyde; m.p. 137°-140° C.; partial NMR: 5.33(2H,s), 7.20(2H,m), 7.52(2H, m), 8.58(2H,d), 10.48(1H,s).

(12) 2-(2-pyridylmethoxy)benzaldehyde; m.p. 67°-68° C.; partial NMR: 5.32(2H,s), 7.06(2H,m), 7.25(1H,m), 7.53(2H,m), 7.75(1H,m), 7.84(1H,dd), 8.61(1H,d), 10.62(1H,s).

(13) 2-(4-nitrobenzyl)benzaldehyde; m.p. 110°-111° C.; partial NMR; 5.31(2H,s), 7.0(1H,d), 7.1(1H,t), 7.59(3H,m), 7.88(1H,dd), 8.28(2H,m), 10.36(1H,s).

(14) 3-benzyloxy-4-methoxybenzaldehyde, obtained as an oil; partial NMR: 5.19(2H,s), 6.99(1H,m), 7.38(7H,m), 9.82(1H,s).

(15) 3-(3cyanobenzyloxy)-4-methoxybenzaldehyde; m.p. 113°-114° C.; partial NMR: 5.20(2H,s), 7.02(1H,d), 7.42(1H,d), 7.49(2H,m), 7.65(2H,m), 7.80(1H,m), 9.83(1H,s).

(16) 4-benzyloxy-3-cyanobenzalehyde; m.p. 117°-118° C.; partial NMR: 5.32(2H,s), 7.14(1H,d), 7.42(5H,m), 8.03(1H,dd), 8.11(1H,d), 9.88(1H,s).

EXAMPLE 46-47

Using an analogous procedure to that described in Example 1, but starting from 4(Z)-6-[(4S,5R)-2,2-dimethyl-4-(3-pyridyl)-1,3-dioxan-5-yl]hexenoic acid and 2-methyl-2-(2-nitro-4-methylphenoxy)propanal and 2-(4-methoxyphenoxy)-2-methylpropanal, respectively, there were obtained:

(Example 46): 4(Z)-6-[(2S,4S,5R)-2-[1-methyl-1-(2-nitro-4-methylphenoxy)ethyl]-4-(3-pyridyl)-1,3-dioxan-5-yl]hexenoic acid, as a solid in 25% yield, with $^{25}$[alpha]$_D$ —117.6° (EtOH, c 0.635); and NMR: 1.45(6H,s), 1.5-1.75(2H,m), 2.2-2.4(8H,m), 3.9-4.2(2H,m), 4.8(1H,s, 5.05-5.5(3H,m), 7.15-7.6(5H,m), 8.4-8.55(2H,m); and (Example 47): 4(Z)-6[(2S,4S,5R)-2-[1-(4-methoxyphenoxy)-1-methylethyl]-4-(3-pyridyl)-1,3-dioxan-5-yl]hexenoic acid, as a solid in 28% yield, with $^{25}$[alpha]$_D$ —122.9° (EtOH, c 0.59); and NMR: 1.35(3H,s), 1.4(3H,s), 1.55-1.8(2H,m), 2.2-2.6(5H,m), 3.75(3H,s), 3.9-4.2(2H,m), 4.75(1H,s), 5.05-5.5(3H,m), 6.75-7.7(6H,m),8.5-8.6(2H,m).

The optically active starting 2,2-dimethyl-1,3-dioxane hexenoic acid derivative was obtained as follows:

(i) A 1.53M solution of butyllithium in hexane (23.9 ml) was added to a solution of 4S-(—)-isopropyl-2-oxazolidinone (4.68 g) in dry THF (75 ml), cooled to —78° C. under argon. The mixtrue was allowed to warm to −50° C. and then stirred for 30 minutes. The mixture was then recooled to −78° C. and a solution of 4-pentenoyl chloride (4.33 g) in dry THF (10 ml) was added dropwise. After the addition, the mixture was stirred at −78° C. for 30 minutes, and then allowed to warm to −20° C. Saturated aqueous ammonium chloride solution (20 ml) was added and the mixture was extracted with ethyl acetate (3×100 ml). The combined organic phases were dried (MgSO₄) and concentrated. The residue was purified by flash column chromatography, eluting with ethyl acetate/hexane 20:80 v/v) to give (4S)-4-isopropyl-3-(4-pentenoyl)oxazolidin-2-one (A) (6.34 g), as an oil; NMR: 0.85–0.95(6H,m), 2.3–2.5(3H,m), 2.9–3.2(2H,m), 4.15–4.5(3H,m), 4.95–5.15 (2H,m), 5.75–6.0(1H,m).

(ii) A 1M solution of dibutylboron triflate in dichloromethane (32.7 ml) was added to a solution of A (6.28 g) in dry dichloromehane (110 ml), cooled to 5° under argon, followed by diisopropylethylamine (6.25 ml). The reaction mixture was stirred at 5° C. for 30 minutes and then cooled to −78° C. 3-Pyridinecarboxaldehyde (3.1 ml) was added dropwise. The mixture was stirred for 30 minutes at −78° C., and then allowed to warm to −50° C. over 30 minutes. The cooling bath was removed and the reaction mixture was stirred at room temperature for 2 hours. The mixture was then cooled to 5° C. and hydrogen peroxide (11.5 ml, 30% w/v aqueous solution) was added. The mixture was stirred for 30 minutes and then poured into water (50 ml) and extracted with dichloromethane (3×100 ml). The combined extracts were dried (MgSO₄) and evaporated. The residue was purified by flash column chromatography, eluting with ethyl acetate/hexane (1:1 v/v, gradually increasing to 100% ethyl acetate), to give (4S)-(3-[(2S)-2-[(1S-1-hydroxy-1-(3-pyridyl)methyl]pent-4-enoyl)-4-isopropyloxazolidin-2-one (B), as a solid, m.p. 112°–113° C. (after recrystallisation from toluene); ²⁵[alpha]_D = +136.0 (EtOH, c 0.311); NMR: 0.85(6H,dd,J=7 Hz), 2.15–2.7(4H,m), 4.0–4.2(2H,m), 4.3–4.55(2H,m), 4.95–5.1(3H,m), 5.65–5.9(1H,m), 7.25–7.35(1H,m), 7.75–7.85(1H,m), 8.5–8.65(2H,m).

(iii) A solution of sodium methoxide (30% w/w) in methanol (3.65 ml) was added to a solution of B (5.76 g) in methanol (40 ml), cooled to 5° C. The mixture was stirred for 15 minutes and then saturated aqueous ammonium chloride solution (10 ml) and ether (50 ml) were added. Sufficient water was added to dissolve any precipitated inorganics and the mixture was then extracted with ether (3×50 ml). The combined extracts were dried (MgSO₄) and evaporated. The residue was purified by flash column chromatography, eluting with ethyl acetate to give methyl (2S)-2-[(1S)-1-hydroxy-1-(3-pyridyl)methyl]pent-4-enoate (C) (3.245 g) as an oil; NMR: 2.3–2.6(2H,m), 2.8–2.9(1H,m), 3.6(3H,s), 4.95–5.1(3H,m), 5.65–5.85(1H,m), 7.25–7.35(1H,m), 7.7–7.75(1H,m), 8.45–8.6(2H,m).

(iv) A solution of C (3.88 g) in THF (10 ml) was added dropwise to a cooled suspension of lithium aluminium hydride (767 mg) in THF (50 ml) at such a rate to maintain the temperature below 10° C. After the additional was complete, the mixture was stirred at 5° C. for 4 hours. Ethyl acetate (20 ml) was added, followed by saturated aqueous ammonium chloride solution (10 ml) and water (10 ml). The mixture was extracted with ethyl acetate (3×50 ml). The combined extracts were dried (MgSO₄) and evaporated. The residue was purified by flash column chromatography, eluting with ethyl acetate, gradually increasing to methanol/ethyl acetate (1:9 v/v), to give (1S,2R)-2-allyl-1-(3-pyridyl)-1,3-propanediol (D) (2.69 g), as an oil; NMR: 1.65–1.8(1H,m), 1.95–2.15(2H,m), 3.15–3.45(2H,m), 4.4–4.5(1H,m), 4.75–5.0(3H,m), 5.25(1H,d,J=7 Hz), 5.6–5.85(1H,m), 7.3–7.4(1H,m), 7.65–7.7(1H,m), 8.4–8.5(2H,m).

(v) p-Toluenesulphonic acid monohydrate (2.91 g) was added to a solution of D (2.68 g) in 2,2-dimethoxypropane (15 ml) and the mixture was stirred for 18 hours. Triethylamine (10 ml) was added and the mixture was partitioned between ether (50 ml) and water (20 ml). The organic layer was dried (MgSO₄) and evaporated. The residue was purified by flash column chromatography, eluting with ethyl acetate/hexane (1:1 v/v) to give (4S,5R)-5-allyl-2,2-dimethyl-4-(3-pyridyl)-1,3-dioxane (E) (2.39 g), as an oil; NMR: 1.53(3H,s), 1.55(3H,s), 1.6–1.75(1H,m), 1.9–2.0(1H,m), 2.3–2.5(1H,m), 3.85–4.2(2H,m), 4.9–5.0(2H,m), 5.27(1H,d,J=3 Hz), 5.45–5.7(1H,m), 7.25–7.35(1H,m), 7.65–7.7(1H,m), (8.5–8.6(2H,m).

(vi) Ozone was passed through a solution of the allyl compound (E) (530 mg) in methanol (30 ml) cooled to −78° C., until a blue colouration was formed. The mixture was purged with argon before methyl sulphide (1.6 ml) was added. The mixture was then stirred at room temperature for 18 hours, before being concentrated in vacuo and partitioned between ether (50 ml) and water (20 ml). The organic layer was dried (MgSO₄) and evaporated. The residue was purified by flash column chromatography, eluting with a mixture of methanol and methylene chloride (5:95 v/v) to give 2-[4S,5R)-2,2-dimethyl-4-(3-pyridyl)-1,3-dioxan-5-yl]acetaldehyde (F), as an oil; NMR: 1.53(3H,s), 1.55(3H,s), 2.15–2.4(2H,m), 2.85–2.95(1H,m), 3.8–3.85(1H,m), 4.25–4.35(1H,m), 5.28(1H,d,J=3 Hz), 7.25–7.7(2H,m), 8.5–8.6(2H,m), 9.6(1H,s).

[Note: The optical purity was assessed as >99% by proton NMR by addition of (R)-(−)-2,2,2-trifluro-1-(9-anthryl)ethanol and observing the region 2.7–2.9 (delta), which showed 4 doublets centred at 2.77, 2.71, 2.82 and 2.85 (1H, CH—CHO)].

(vii) The acetaldehyde (F) is then converted to 4(Z)-6-[(4S,5R)-2,2-dimethyl-4-(3-pyridyl)-1,3-dioxane-5-yl]hexenoic acid, having ²⁵[alpha]_D −113.3 (EtOH, c 0.465) and NMR essentially identical with that of the racemic material described in Example 1, using an analogous procedure to that described in the prior (v) of Example 1.

EXAMPLE 48 p-Toluenesulphonic acid monohydrate (409 mg) was added to a stirred solution of 4(Z)-6-[2,2-dimethyl-4-(3-pyridyl)-1,3-dioxan-cis-5-yl]hexenoic acid (570 mg) and 2-(2-cyano-4-methylphenoxy)-2-methylpropanal (568 mg) in acetonitrile (5 ml), and the mixture was stirred for 18 hours at 80° C. Water (40 ml) and 2M sodium hydroxide solution (4 ml) were added and the mixture washed with ether (2×20 ml). The aqueous phase was acidified with acetic acid and extracted with ethyl acetate (3×25 ml). The extracts were washed with saturated brine (2×15 ml), dried (MgSO₄) and evaporated. The residual gum was purified by MPLC, eluting with ethyl acetate/hexane/acetic acid (70:30:1 v/v) to give 4(Z)-6-[(2,4,5-cis)-2-(1-(2-cyano-4-methylphenoxy)-1-methylethyl)-4-(3-pyridyl)-1,3-dioxan-5-yl]hexenoic acid hemi-hydrate (249 mg), as a white foam; NMR: 1.48(3H,s), 1.50(3H,s), 1.57(1H,m), 1.72(1H,m), 2.09(0.75H,s), 2.27(4H,m), 2.30(3H,s), 2.43(1H,m), 4.02(1H,dm J=11 Hz), 4.19(1H,dd, J=11, 1.5 Hz), 4.98(1H,s), 5.18(1H,d J=2 Hz), 5.25(1H,m), 5.41(1H,m), 5.77(1H,b), 7.09(1H,d, J=9 Hz), 7.28(3H,m), 7.57(1H,dm J=8 Hz), 8.45(1H,bs), 8.51(1H,bd J=4 Hz); microanalysis found: C, 68.0; H, 6.5; N, 6.0%; $C_{26}H_{30}N_2O_5.\frac{1}{2}H_2O$ requires: C, 68.0; H, 6.7; N, 6.1%; m/e 451 (M+H)+.

The necessary starting aldehyde was obtained as follows:

(i) Anhydrous potassium carbonate (14.0 g) was added to a stirred solution of 2-bromo-4-methylphenol (19.0 g) and ethyl 2-bromo-2-methylpropionate (27.7 g) in 2-butanone (80 ml) and the mixture heated at reflux for 3 hours, then cooled to ambient temperature and added to water (400 ml). This mixture was extracted with ether (1×300 ml, 2×150 ml) and the combined extracts washed with 1M sodium hydroxide solution (2×100 ml), water (2×100 ml) and saturated brine (1×100 mml), then dried (MgSO4) and the solvent removed by evaporation. The residual oil was distilled under reduced pressure to give ethyl 2-(2-bromo-4-methylphenoxy)-2-methylpropionate (A) (18.7 g), as an oil; b.p. 116°-118° C. at 0.5 mm Hg; NMR: 1.28 (3H,t J=7 Hz), 1.60(6H,s), 2.26(3H,s), 4.26(2H,q J=7 Hz), 6.78(1H,d J=8 Hz), 6.96(1H,dd J=8, 1.5 Hz), 7.35(1H,d J=1.5 Hz); m/e 318 (M+NH4)+.

(ii) Cuprous cyanide (3.76 g) was added to a stirred solution of A (10.54 g) in dimethylformamide (20 ml) and then heated at reflux temperature (bath temperature 180° C.) for 4.5 hours. After cooling the residue was added to a stirred solution of ferric chloride/12M hydrochloric acid/water (14 g: 3.5 ml: 55 ml) and stirring continued for 30 minutes. This solution was extracted with dichloromethane (1×100 ml, 2×50 ml) and the combined extracts washed with water (3×50 ml), then dried (MgSO4) and the solvents removed in vacuo. The residue was purified by MPLC, eluting with 10% v/v ethyl acetate in hexane to give ethyl 2-(2-cyano-4-methylphenoxy)-2-methylpropionate (B) (7.01 g) as a colourless oil which crystallised slowly on keeping at 4° C.; m.p. 54°-56° C., NMR: 1.24(3H,t J=7 Hz), 1.65(6H,s), 2.91(3H,s), 4.23(2H,q J=7 Hz), 6.74(1H,d J=9 Hz), 7.21(7.35(1H,d J=2 Hz); m/e 265(M+NH4)+.

(iii) A stirred solution of B (2.47 g) in dry toluene (40 ml) under argon was cooled to −70° C. and treated dropwise with 1.5M diisobutylaluminium hydride in toluene (7.3 ml). Stirring was continued for a further 30 minutes at −70° C. when a 10% v/v methanol in toluene solution (2 ml) was added and the mixture warmed to ambient temperature. The solution was added to a vigorously stirred ice-water mixture (50 ml), stirred for 2 hours and then filtered through kieselguhr. The organic phase was separated and the aqueous phase extracted with ether (2×75 ml). The combined organic phases were washed with saturated brine (2×40 ml), dried (MgSO4) and evaporated. Purification of the residue by MPLC, eluting with 10% v/v ethyl acetate in hexane gave an oil which slowly crystallised. Trituration with hexane and filtration gave 2-(2-cyano-4-methylphenoxy)-2-methylpropanal (600 mg); m.p. 60°-64° c.; NMR: 1.50(6H,s), 2.31(3H,s), 6.74(1H,d J=9 Hz), 7.26(1H,m), 7.39(1H,d J=2 Hz), 9.83(1H,s); m/e 221 (M+NH4)+.

EXAMPLE 49

In a similar manner to Example 48, but starting from 2-(2-cyano-5-methylphenoxy)-2-methylpropanal instead of 2-(2-cyano-4-methylphenoxy)-2-methylpropanal and heating the reaction for 48 hours instead of 18 hours there was obtained 4(Z)-6-[(2,4,5-cis)-2-(1-(2-cyano-5-methylphenoxy)-1-methylethyl)-4-(3-pyridyl)-1,3-dioxan-5-yl]hexenoic acid hemihydrate (17%) as a white foam; NMR: 1.49(3H,s), 1.52(3H,s), 1.59(1H,m), 1.73(1H,m), 2.28(4H,m), 2.36(3H,s), 2.43(1H,m), 4.03(1H,dm J=11 Hz), 4.20(1H,dd J=11, 1 Hz), 4.97(1H,s), 5.17(1H,d J=2 Hz), 5.23(1H,m), 5.41(1H,m), 6.92(1H,dd J=7.1 Hz), 7.02(1H,s), 7.30(1H,m), 7.36(1H,d J=7 Hz), 7.57(1H,m), 8.49(2H,m); microanalysis found: C, 68.1; H, 6.5; N, 5.9%; $C_{26}H_{30}N_2O_4.\frac{1}{2}H_2O$, requires: C, 68.0; H, 6.7; N 6.1%; m/e 451 (M+H)+.

The necessary aldehyde was prepared as follows:

(i) In a similar manner to Example 48(i), but starting with 2-chloro-5-methylphenol instead of 2-bromo-4-methylphenol and heating at reflux for 18 hours instead of 3 hours there was obtained ethyl 2-(2-chloro-5-methylphenoxy)-2-methylpropionate (72%) as a colourless oil; b.p. 109°-110° C. at 0.5 mm Hg; NMR: 1.28(3H,t J=7 Hz), 1.60(6H,s), 2.26(3H,s), 4.26(2H, q J=7 Hz), 6.72(2H,m), 7.21(1H,d J=7 Hz); m/e 274 (M+NH4)+.

(ii) In a similar manner to Example 48(ii), but starting from ethyl 2-(2-chloro-5-methylphenoxy)-2-methylpropionate instead of ethyl 2-(2-bromo-4-methylphenoxy)-2-methylpropionate and using DMPU as solvent in place of dimethylformamide and heating for 18 hours at 200° C. there was obtained, after evaporation of the dichloromethane extracts a liquid. This was dissolved in ether (200 ml) and the solution washed with water (3×50 ml) to removed the DMPU, then dried (MgSO4) and evaporated. The residue was purified by MPLC, eluting with 10% v/v ethyl acetate in hexane to give ethyl 2-(2-cyano-5-methylphenoxy)-2-methylpropionate (38%) as a colourless oil; NMR (250 MHz, CDCl3): 1.24(3H,t J=7 Hz), 1.67(6H,s), 2.33(3H,s), 4.24(2H, q J=7 Hz), 6.60(1H,s), 6.84(1H,dm, J=8 Hz), 7.44(1H,d J=8 Hz); m/e 265 (M+NH4)+.

(iii) In a similar manner to Example 48(iii), but starting from ethyl 2-(2-cyano-5-methylphenoxy)-2-methylpropionate instead of ethyl 2-(2-cyano-4-methylphenoxy)-2-methylpropionate there was obtained 2-(2-cyano-5-methylphenoxy)-2-methylpropanal (28%), as a crystalline solid; m.p. 57°-59° C.; NMR (250 MHz, CDCl3): 1.53(6H,s), 2.34(3H,s), 6.62(1H,s), 6.91(1H,d J=8 Hz), 7.47(1H,d J=8 Hz), 9.34(1H,s); m/e 221 (M+NH4)+.

EXAMPLE 50

Using a similar procedure to that described in Example 48, but starting from 2-(2-cyano-4-methoxyphenoxy)-2-methylpropanal instead of 2-(2-cyano-4-methylphenoxy)-2-methylpropanal, there was obtained 4-(Z)-6[(2,4,5-cis)-2-(1-(2-cyano-4-methoxyphenoxy)-1-methylethyl)-4-(3-pyridyl)-1,3-dioxan-5-yl]hexenoic acid, in 10% yield; m.p. 130°-140° C.; NMR: 1.46(3H,s), 1.48(3H,s), 1.58(1H,m), 2.26(4H,m), 2.42(1H,m), 3.76(3H,m), 4.03(1H,dm J=11 Hz), 4.20(1H,dd J=11, 1.5 Hz), 4.97(1H,s) 5.17(1H,d J=2 Hz), 5.24(1H,m), 5.40(1H,m), 6.93(1H,d J=2.5 Hz), 7.02(1H,dd J=8, 2.5), 7.12(1H,d J=8 Hz), 7.30(1H,m), 7.57(1H,m), 8.50(2H, m); microanalysis found: C, 66.5; H, 6.2; N, 5.8%; $C_{26}H_{30}N_2O_6$ requires: C, 66.9; H, 6.5; N, 6.0%; m/e 467 (M+H)+.

The starting aldehyde was prepared as follows:

(i) 2M sodium hydroxide solution was slowly added to a stirred solution of 2-hydroxy-5-methoxybenzaldehyde (9.4 g) and hydroxylamine hydrochloride (5.37 g) in methanol (100 ml) until the pH was 7. Stirring was continued for a further 20 minutes and the mixture was then added to water (600 ml). After cooling at about 4° C. for 2 hours, the white solid was collected by filtration, washed with water and dried to give 2-hydroxy-5-methoxybenzaldoxine (A) (9.84 g) as white crystals; m.p. 119°–120° C., NMR: 3.77(3H,s), 6.70(1H,d J=2 Hz), 6.90(2H,m), 7.47(1H,s), 8.19(1H,s), 9.39(1H,b); m/e 168(M+H)+.

(ii) A solution of A (9.84 g) in acetic anhydride (50 ml) was heated for 6 hours under reflux. The mixture was left overnight at ambient temperature and was then added to a vigorously stirred ice-water mixture (400 ml). After 1 hour, the resulting solid was collected by filtration. 2M Sodium hydroxide solution (150 ml) was added to a stirred solution of this solid in methanol (50 ml). Stirring was continued for 1 hour. The clear solution obtained was washed with ether (50 ml), acidified with 2M hydrochloric acid solution to pH4 and extracted with ethyl acetate (3×50 ml). The combined extracts were washed with water (20 ml), then saturated brine (20 ml), dried (MgSO$_4$) and the solvent removed by evaporation to give 2-cyano-4-methoxyphenol (B) (783 g) as a white solid, m.p. 128°–138° C.; NMR (250 MHz, CDCl$_3$/DMSOd$_6$): 3.66(3H,s), 6.86(3H,m); m/e 167 (M+N$_{H4}$)+.

(iii) Anhydrous potassium carbonate (1.38 g) was added to a stirred solution of B (745 mg) and 2-bromo-2-methylpropanal (755 mg) in tetrahydrofuran (20 ml). The mixture was heated under reflux for 1 hour and then left overnight at ambient temperature. Water (20 ml) was added and the mixture extracted with ether (2×20 ml). The combined extracts were washed with water (2×10 ml), then saturated brine (10 ml) and dried (MgSO$_4$). Evaporation of the solvent and purification of the residual oil by medium pressure chromatography (MPLC), eluting with 25% v/v ethyl acetate in hexane, gave 2-(2-cyano-4-methoxyphenoxy)-2-methylpropanal (677 mg) as a colourless oil; NMR 1.47(6H,s), 3.80(3H,s), 6.83(1H,d J=9 Hz), 7.03(2H,m), 9.86(1H,s); m/e 237 (M+NH$_4$)+.

EXAMPLE 51

An analogous hydrolysis procedure was used to that described in Example 12, but starting from methyl 4(Z)-6-[(2,4,5-cis)-2-phenyldifluoromethyl-4-(3-pyridyl)-1,3-dioxan-5-yl]hexenoate. Evaporation of the extracts of the acidified reaction mixture gave a pale yellow oil, which solidified on trituration with hexane. Recrystallisation from ethyl acetate/hexane gave 4(Z)-6[(2,4,5-cis)-2-phenyldifluoromethyl-4-(3-pyridyl)-1,3-dioxan-5-yl]hexenoic acid (58%; m.p. 146°–148° C.; NMR: 1.34(1H,m), 1.64(1H,m), 1.99(3H,m), 2.23(2H,m), 3.96(1H,bd J=11 Hz), 4.13(1H,bd J=11 Hz), 5.09(3H,m), 5.35(1H,m), 7.13(1H,m), 7.46(3H,m), 7.60(3H,m), 8.51(2H,m); microanalysis found: C,65,4; H,5.8; N,3.5%; C$_{22}$H$_{23}$N$_{F2}$O$_4$ requires: C,65.5; H,5.7; N,3.5%; m/e 404 (M+H)+.

The starting ester was prepared as follows:

(i) A stirred solution ethyl alpha,alpha-difluorophenylacetate (1.0 g) (prepared according to Middleton and Bingham, J. Org. Chem., 1980 45, 2883) in dry toluene (15 ml) under argon was cooled to −70° C. and treated dropwise with 1.5M diisobutylaluminium hydride in toluene (3.5 ml) over 15 minutes. Stirring was continued for a further 1 hour at −70° C. when methanol (1 ml) was added. The solution was allowed to warm to ambient temperature and added to a vigorously stirred ice-water mixture. Stirring was continued for 2 hours, the mixture filtered through kieselguhr and the phases separated. The aqueous phase was extracted with ethyl acetate (3×25 ml) and the combined organic phases washed with saturated brine (2×20 ml), then dried (MgSO$_4$) and evaporated to give an oil. MPLC, eluting with 20% v/v ethyl acetate in hexane gave 760 mg of a colourless oil (A) which was shown by NMR to be a mixture of alpha, alpha-difluorophenylacetaldehyde and the corresponding hydrate and hemiacetal thereof.

(ii) In a similar manner to Example 12(iv), but using the aldehyde mixture A instead of hexafluoroacetone sesquihydrate and using 60% v/v ethyl in hexane as eluant in the chromatographic purification, there was obtained methyl 4(Z)-6-[(2,4,5-cis)-2-(phenyldifluoromethyl)-4-(3-pyridyl)-1,3-dioxan-5-yl]hexenoate as a waxy solid (31%); NMR: 1.30(1H,m), 1.54(1H,m), 1.98(3H,m), 2.20(2H,m), 3.57(3H,s), 3.97(1H,dm J=11 Hz), 4.14(1H,d J=11 Hz), 5.08(3H,m), 5.31(1H,m), 7.33(1H,m), 7.47(3H,m), 7.61(3H,m), 8.49(1Hd J=1 Hz), 8.54(1H,dd J=4,1 Hz); m/e 418 (M+H)+.

EXAMPLE 52

Using a similar procedure to that described in Example 1, but using 2-methyl-2-(2-methylsulphonylphenoxy)propanal as the aldehyde, there was obtained 4(Z)-6-[(2,4,5-cis)-2-(1-methyl-1-(4-methylsulphonylphenoxy)ethyl)-4-(3-pyridyl)-1,3-dioxan-5-yl]hexenoic acid, as an oil in 29% yield; NMR: 1.6(6H,s), 1.7–2.6(7H,m), 3.2(3H,s), 4.0–4.25 (2H,m), 5.1(1H,s), 5.2–5.5(3H,m), 7.1–8.0(6H,m), 8.5–8.6(2H,m).

The necessary aldehyde was obtained starting from 2-(methylthio)phenol in an analogous manner to that described for 2-methyl-2-(4-methylsulphonylphenoxy)propanal in Example 16. 2-Methyl-2-(2-methylsulphonylphenoxy)propanal was obtained as a solid in 51% yield (from carboxylate); NMR: 1.55(6H,s), 3.25(3H,s), 6.85–7.55(3H,m), 8.0–8.5(1H,m), 9.85(1H,s), with isolation of the following intermediates:

(a) ethyl 2-methyl-2-(2-(methylthio)phenoxy)propionate: oil (38% yield from the phenol); NMR: 1.25(3H,t J=7 Hz), 1.6(6H,s), 2.4(3H,s), 4.25(2H,q J=7 Hz), 6.7–7.2(4H,m); and (b) ethyl 2-methyl-2-(2-methylsulphonylphenoxy)propionate: oil [89% yield from (a)]; 1.25(3H,t J=7 Hz), 1.7(6H,s), 3.25(3H,s), 4.3(2H,q J=7 Hz), 6.9–7.55(3H,m), 7.95–8.05(1H,m).

EXAMPLES 53–54

Using a similar procedure to that described in Example 1 but using 2-methyl-2-(2-methylthiophenoxy)propanal and 2-methyl-2-(4-methylthiophenoxy)propanal, respectively, there were obtained:

(Example 53): 4(Z)-6-[(2,4,5-cis)-2-(1-methyl-1-(2-methylthiophenoxy)ethyl-4-(3-pyridyl)-1,3-dioxan-5-yl]hexenoic acid, as a solid in 45% yield; NMR: 1.45(3H,s), 1.5(3H,s), 1.55(2H,m), 2.2–2.5(8H,m), 4.0–4.25(2H,m), 5.0(1H,s), 5.1–5.5(3H,m), 7.0–7.7(6H,m), 8.5–8.6(2H,m); and (Example 54): 4(Z)-6-[(2,4,5-cis)-2-(1-methyl-1-(2-methylthiophenoxy)ethyl)-4-(3-pyridyl)-1,3-dioxan-5-yl]hexenoic acid, as a solid in 26% yield; NMR: 1.35(3H,s), 1.4(3H,s), 1.6–1.8(2H,m), 2.2–2.5(8H,m), 3.95–4.25(2H,m), 4.75(1H,s), 5.1–5.5(3H,m), 6.9–7.75(6H,m), 8.5–8.6(2H,m).

The starting aldehydes were obtained in an analogous manner to that described for 2-methyl-2-(4-methylsulphonylphenoxy)propanal in Example 16:

(a) 2-methyl-2-(2-methylthiophenoxy)propanal, isolated as an oil; NMR: 1.45(6H,s), 2.4(3H,s), 6.7-7.2(4H,m), 9.9(1H,s); in 53% yield, by reduction of ethyl 2-methyl-2-(2-methylthiophenoxy)propionate; and (b) 2-methyl-2-(4-methylthiophenoxy)propanal, isolated as an oil; NMR: 1.4(6H,s), 2.45(3H,s), 6.75-7.25(4H,m), 9.85(1H,s).

EXAMPLE 55

Using an analogous procedure to that described in Example 1, but using from 2-thiophenoxybenzaldehyde as the aldehyde, there was obtained 4(Z)-6-[2,4,5-cis)-4-(3-pyridyl)-2-(2-thiophenoxyphenoxy)-1,3-dioxan-5-yl]hexenoic acid, as a solid in 26% yield; NMR: 1.7-1.9(2H,m), 2.2-2.5(5H,m), 4.1-4.3(2H,m), 5.2-5.5(3H,m), 6.15(1H,m), 7.1-7.9(11H,m), 8.45-8.6(2H,m).

the 2-thiophenoxybenzaldehyde was made in known manner from 2-fluorobenzaldehyde and thiophenol.

EXAMPLES 56-57

Using an analogous procedure to that described in Example 1, but starting from 2-methyl-2-(2-nitro-4-methoxyphenoxy)-propanal and 2-methyl-2-(2-methyl-6-nitrophenoxy)propanal, respectively, there were obtained:

(Example 56): 4(Z)-6-[(2,4,5-cis)-2-(1-methyl)-1-(2-nitro-4-methoxyphenoxy)ethyl)-4-(3-pyridyl)-1,3-dioxan-5-yl]hexenoic acid, as a solid in 10% yield; NMR: 1.35(6H,s), 1.45-1.7(2H,m), 2.1-2.4(5H,m), 3.75(3H,s), 3.85-4.1(2H,m), 4.75(1H,s), 5.0-5.4(3H,m), 6.9-7.55(5H,m), 8.4-8.5(2H,m); and (Example 57): 4(Z)-6-[(2,4,5-cis)-2-(1-methyl)-1-(2-methyl-6-nitrophenoxy)ethyl-4-(3-pyridyl)-1,3-dioxan-5-yl]hexenoic acid, as a solid in 7% yield; NMR: 1.25(3H,s), 1.3(3H,s), 1.45-1.65(2H,m), 2.05-2.4(8H,m), 3.8-4.05(2H,m), 4.7(1H,s), 5.0-5.5(3H,m), 6.95-7.5(5H,m), 8.35-8.5(2H,m).

The starting aldehydes were obtained in an analogous manner to that described for 2-methyl-2-(4-methylsulphonylphenoxy)propanal in Example 16:

(a) 2-methyl-2-(2-nitro-4-methoxyphenoxy)propanal, isolated as an orange oil; NMR; 1.45(6H,s), 3.8(3H,s), 6.9-7.3(3H,m), 9.85(1H,s); in 41% yield by reduction of ethyl 2-methyl-2-(2-nitro-4-methoxyphenoxy)propionate, itself obtained as an oil; NMR: 1.3(3H,t J=7 Hz), 1.6(6Hs,), 3.8(3H,s), 4.25(2H,q J=7 Hz), 7.0-7.3(3H,m); in 8% yield, by alkylation of 4-methoxy-2-nitrophenoxol; and (b) 2-methyl-2-(2-methyl-6-nitrophenoxy)propanal, isolated as a yellow oil; NMR: 1.35(6H,s), 2.3(3H,s), 7.1-7.6(3H,m), 9.85(1H,s); in 65% yield, by reduction of ethyl 2-methyl-2-(2-methyl-6-nitrophenoxy)propionate, itself obtained as an oil; NMR: 1.35(3H,t J=7 Hz), 1.5(6H,s), 2.3(3Hs,), 4.25(2H,q J=7 Hz), 7.05-7.55(3H,m); in 8% yield, by alkylation of 2-methyl-6-nitrophenol.

EXAMPLE 58

Using a similar procedure to that described in Example 1, but using 2-benzoylbenzaldehyde as the aldehyde, there was obtained 4(Z)-6-[(2,4,5-cis)-2-(2-benzoylphenyl)-4-(3-pyridyl)-1,3-dioxan-5-yl]hexenoic acid, as a solid in 64% yield; NMR: 1.15-1.45(2H,m), 1.85-2.25(5H,m), 3.6-3.9(2H,m), 4.7-5.3(3H,m), 5.55(1H,m), 6.8-7.65(11H,m), 8.05-8.2(2H,m).

the 2-benzoylbenzaldehyde was obtained as a solid in 82% yield: NMR: 7.4-8.1(9H,m), 10.05(1H,s), by oxalyl chloride/dimethyl sulphoxide oxidation at −50° C. to ambient temperature of 2-(alpha-hydroxybenzyl)benzyl alcohol, itself obtained as a solid in 26%; NMR: 2.95(1H,bs s), 4.45-4.65(2H,m), 6.05(1Hs,), 7.2-7.4(9H,m); by lithium aluminium hydride reduction of 2-benzoylbenzoic acid.

EXAMPLES 59-60

Using an analogous procedure to that described in Example 23 but starting from the appropriate benzaldehyde of the formula R$^1$.CHO the following compounds were obtained:

(Example 59): 4(Z)-6-[(2,4,5-cis)-2-(1-methyl-1-(phenylthio)ethyl)-4-(3-pyridyl)-1,3-dioxan-5-yl]hexenoic acid, as a colourless solid, m.p. 118°-120° C.; NMR: 1.32(6H,s), 1.65(2H,m), 2.31(5H,m), 3.90(1H,d), 4.18(1H,d), 4.55(1H,s), 5.00(1H,d), 5.22(1H,m), 5.40(1H,m), 5.70(1H,m), 7.28(4H,m), 7.53(2H,m), 7.62(1H,d), 8.50(2H,m), m/e 428 (M+H)$^+$; in 63% yield, starting from 2-methyl-2-(phenylthio)propanal; and (Example 60): 4(Z)-6-[(2,4,5-cis)-2-(1-methyl-1-(4-fluorophenylthio)ethyl)-4-(3-pyridyl)-1,3-dioxan-5-yl]hexenoic acid, as a colourless solid, m.p. 109°-111° C.; NMR: 1.33(6H,s), 1.64(2H,m), 2.34(5H,m), 3.90(1H,m), 4.18(1H,m), 4.56(1H,s), 5.02(1H,d), 5.31(2H,m), 6.94(2H,m), 7.35(1H,m), 7.55(3H,m), 8.52(2H,m); m/e 444 (M−H)$^+$; in 61% yield starting from 2-methyl-2-(4-fluorophenylthio)propanal.

The starting benzaldehydes were obtained using a similar procedure to that described in part (vii) of Example 1 and had the following properties:

(a) 2-methyl-2-(phenylthio)propanal: obtained in 40% yield as an oil, NMR: 1.25(6H,s), 7.25(5H,m), 9.28(1H,s); m/e 194(M+NH$_4$)$^+$; starting from phenylthiol and 1,1-dichloro-2-hydroxy-2-methylpropane; and (b) 2-methyl-2-(4-fluorophenylthio)propanal: obtained in 14% yield as an oil, NMR: 1.31(6H,s), 6.99(2H,m), 7.36(2H,m), 9.28(1H,s); m/e 216(M+NH$_4$)$^+$; starting from 4-fluorophenylthiol and 1,1-dichloro-2-hydroxy-2-methylpropane.

EXAMPLE 61

The acid catalysed aldehyde/ketone exchange reactions described in any of the preceding Examples 23-60, may also be performed using 4(Z)-6-[2,2-diethyl-4-(3-pyridyl)-1,3-dioxan-cis-5-yl]hexenoic acid (described in Example 14) instead of the 2,2-dimethyl derivative [compound (A) described in part (v) of Example 1]. In general largely similar yields of compounds of the formula I may be obtained.

EXAMPLE 62

Illustrative pharmaceutical dosage forms suitable for presenting the compounds of the invention for therapeutic or prophlactic use include the following tablet, capsule, injection and aerosol formulations, which may be obtained by conventional procedures well known in the art of pharmacy and are suitable for therapeutic or prophylactic use in humans:

| (a) Tablet I | mg/tablet |
|---|---|
| Compound Z* | 1.0 |

| -continued | |
|---|---|
| Lactose Ph. Eur. | 93.25 |
| Croscarmellose sodium | 4.0 |
| Maize starch paste (5% w/v aqueous paste) | 0.75 |
| Magnesium stearate | 1.0 |

| (b) Tablet II | mg/tablet |
|---|---|
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |

| (c) Tablet III | mg/tablet |
|---|---|
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |

| (d) Capsule | mg/capsule |
|---|---|
| Compound Z* | 10 |
| Lactose Ph. Eur. | 488.5 |
| Magnesium stearate | 1.5 |

| (e) Injection I (50 mg/ml) | |
|---|---|
| Compound Z* (free acid form) | 5.0% w/v |
| 1 M Sodium hydroxide solution | 15.0% v/v |
| 0.1 M Hydrochloric acid (to adjust to pH 7.6) | |
| Polyethylene glycol 400 | 4.5% w/v |
| Water for injection | to 100% |

| (f) Injection II (10 mg/ml) | |
|---|---|
| Compound Z* (free acid form) | 1.0% w/v |
| Sodium phosphate EP | 3.6% w/v |
| 0.1 M Sodium hydroxide solution | 15.0% v/v |
| Water for injection | to 100% |

| (g) Injection III (1 mg/ml, buffered to pH 6) | |
|---|---|
| Compound Z* (free acid form) | 0.1% w/v |
| Sodium phosphate BP | 2.26% w/v |
| Citric acid | 0.38% w/v |
| Polyethylene glycol 400 | 3.5% w/v |
| Water for injection | to 100% |

| (h) Aerosol I | mg/ml |
|---|---|
| Compound Z* | 10.0 |
| Sorbitan trioleate | 13.5 |
| Trichorofluoromethane | 910.0 |
| Dichlorodifluoromethane | 490.0 |

| (i) Aerosol II | mg/ml |
|---|---|
| Compound Z* | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound Z* | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound Z* | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note
*The active ingredient Compound Z is a compound of formula I, or a salt thereof, for example a compound of formula I described in any of the preceding Examples, and especially as described in Example 18, 19, 20, 46 or 48.

The tablet compositions (a)–(c) may be enteric coated by conventional means, for example, with cellulose acetate phthalate. The aerosol compositions (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE
(in description)

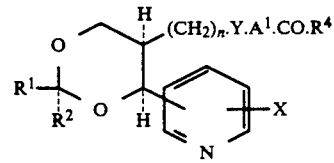

I

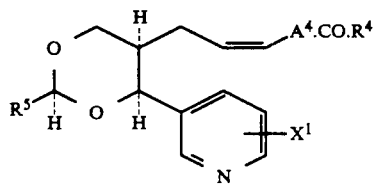

II

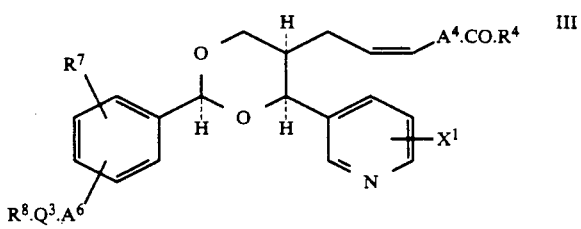

III

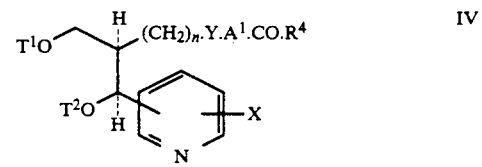

IV

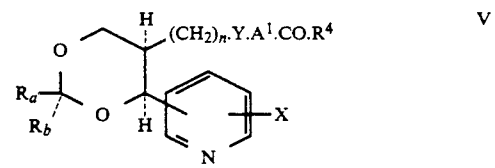

V

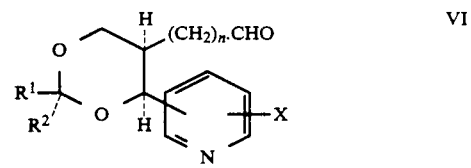

VI

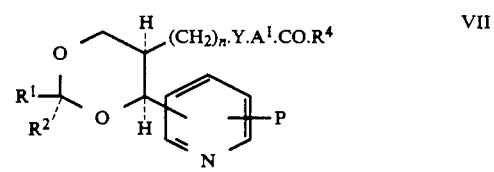

VII

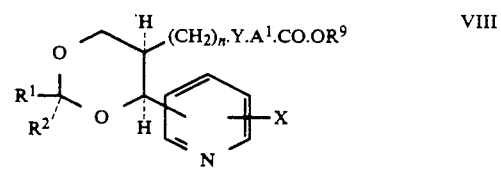

VIII

-continued
CHEMICAL FORMULAE
(in description)

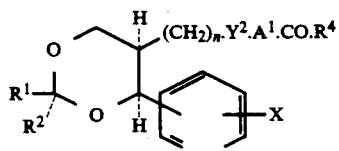 IX

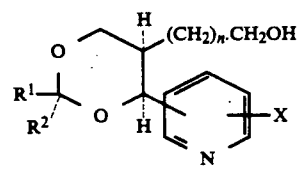 X

L.A$^1$.CO.R$^4$    XI

-continued
CHEMICAL FORMULAE
(in description)

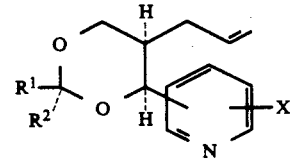 XII

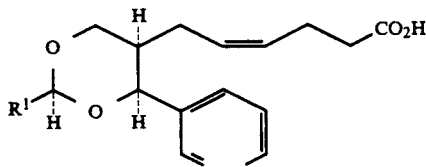 XIII

SCHEME 1

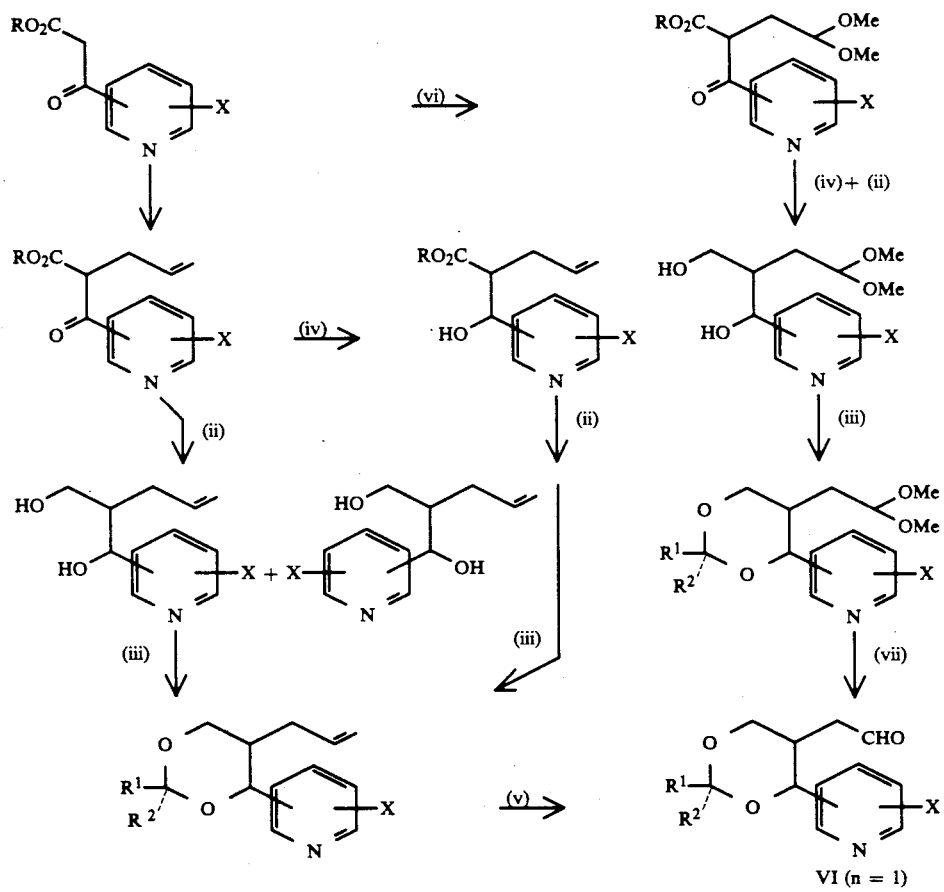

Reagents:
(i) NaOEt, EtOH, allyl bromide
(ii) LiAlH$_4$ or LiBH$_4$, THF
(iii) TsOH, R$^1$R$^2$.CO or R$^1$R$^2$.C(OMe)$_2$
(iv) Zn(BH$_4$)$_2$, Et$_2$O
(v) O$_3$, CH$_2$Cl$_2$, then Ph$_3$P; or OsO$_4$, NaIO$_4$, t-BuOH, H$_2$O
(vi) NaH, DMSO, BrCH$_2$CH(OMe)$_2$
(vii) H$^+$, H$_2$O Note:
R = (1-4C)alkyl, such as methyl (Me) or ethyl (Et);
Ts = p-toluenesulphonyl

SCHEME 2
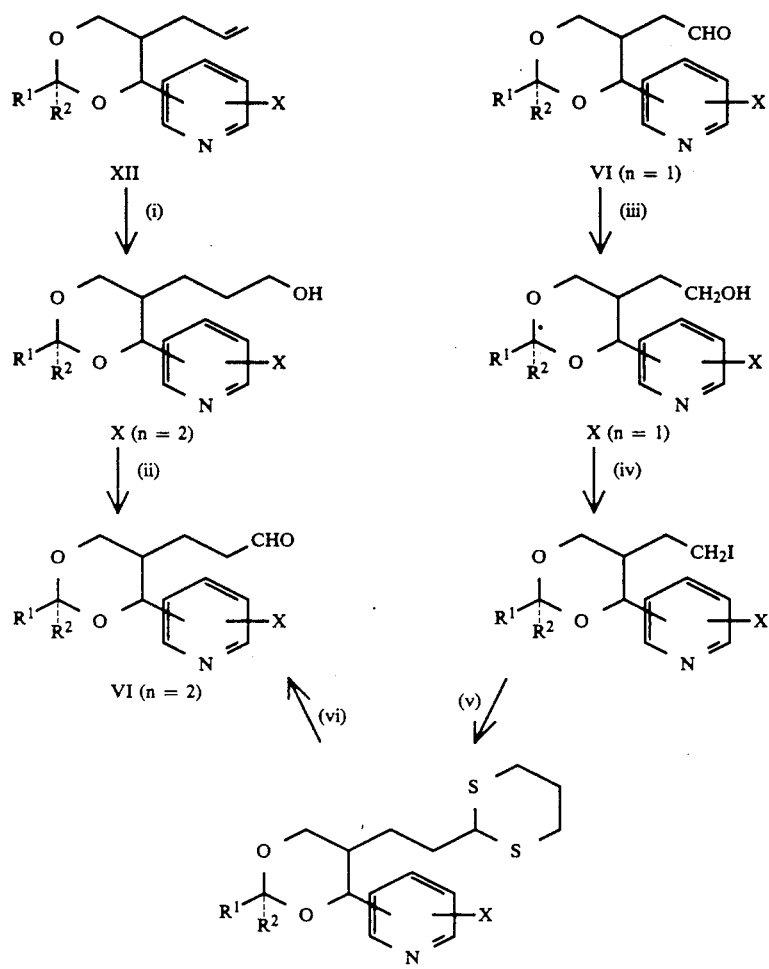
Reagents:
(i) $B_2H_6$ then $H_2O_2$
(ii) Pyridinium chlorochromate, $CH_2Cl_2$ or DCCI, DMSO, pyridine, TFA
(iii) $NaBH_4$, EtOH;
(vi) Ammonium cerium(IV) nitrate, 0° C.
(iv) TsCl, pyridine; then NaI/acetone, 40–60° C.
(v) 1,3-dithiane, LiN(i-Pr)$_2$, THF at −78° C.
SCHEME 3
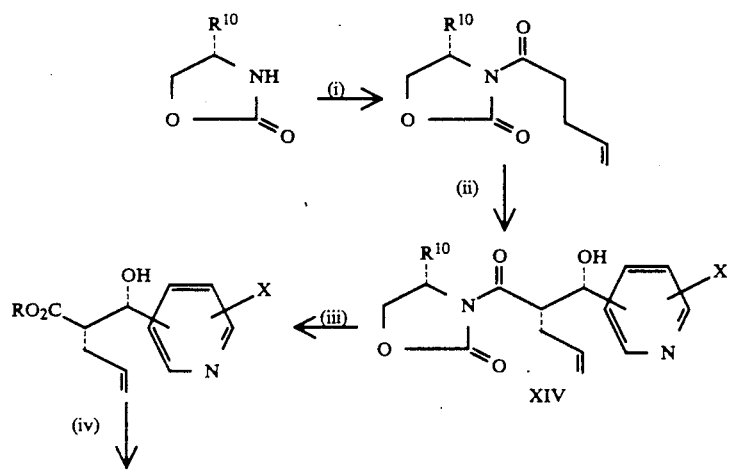

SCHEME 3

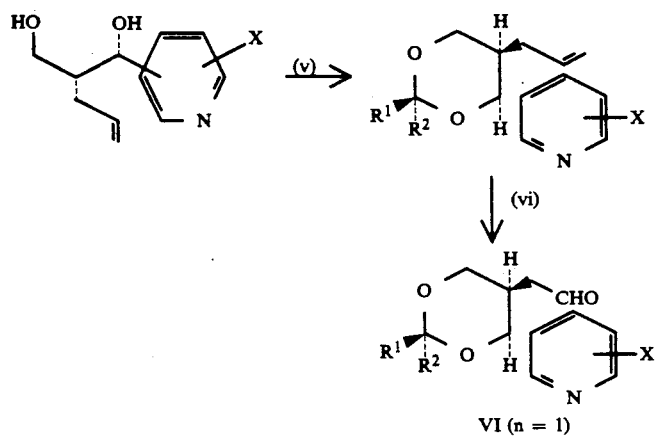

Reagents:
(i) pentenoyl chloride/BuLi/THF/−78° C.
(ii) Bu$_2$B.SO$_2$CF$_3$/(i-Pr)$_2$NEt/pyridinecarboxaldehyde/CH$_2$Cl$_2$; H$_2$O$_2$/pH7
(iii) NaOR/ROH [R = (1–4C)alkyl such as Me]
(iv) LiAlH$_4$/THF
(v) R$^1$R$^2$.CO/p-toluenesulphonic acid (p-Ts.OH)
(vi) O$_3$/CH$_2$Cl$_2$, then Me$_2$S or Ph$_3$P

SCHEME 4

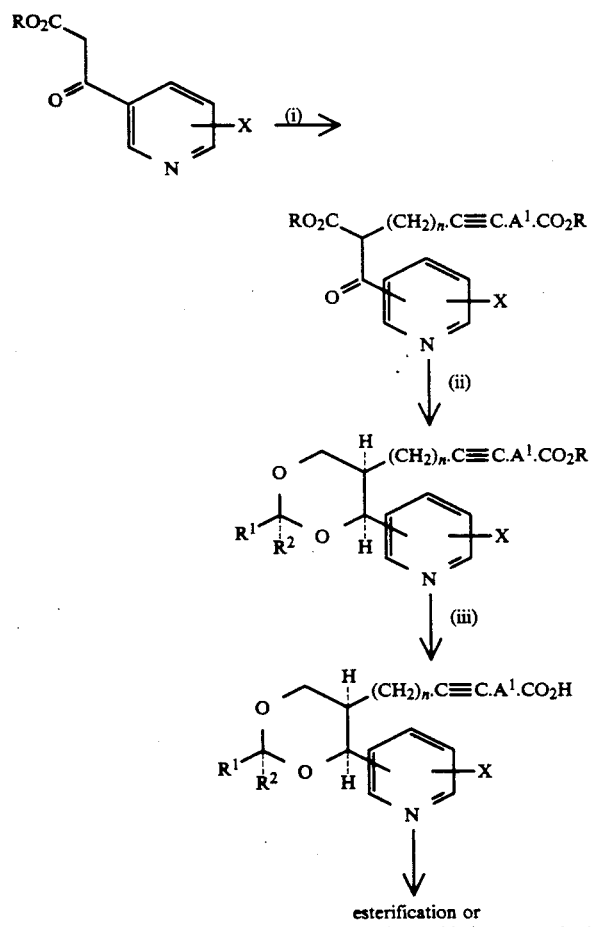

Reagents:
(i) NaOEt, EtOH, Br(CH$_2$)$_n$.C≡C.A$^1$.CO$_2$R
(ii) NaBH$_4$; then R$^1$R$^2$CO, TsOH
(iii) NaOR/ROH
[R = (1–4C)alkyl such as Me]

What is claimed is:

1. A 1,3-dioxane alkenoic acid derivative of the formula I

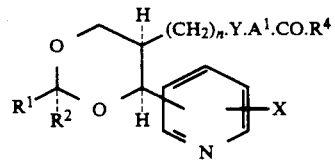

wherein: n is the integer 1 or 2; X is hydrogen, hydroxy or (1–4C)alkoxy; Y is methyleneoxy, vinylene or ethylene; A$^1$ is (1–6C)alkylene; and a) R$^2$ is hydrogen, and R$^1$ is naphthyl or phenylthio(1–6C)alkyl optionally bearing 1 to 2 substituents selected from halogeno, cyano, nitro, (1–4C)alkyl, (1–4C)alkoxy and trifluoromethyl, or R$^1$ is a group of the formula R$^3$.A$^2$—, in which:

R$^3$ is phenyl bearing a substituent which is selected from (1–4C)alkyl, (1–4C)alkoxy, hydroxy, (2–5C)alkenyl, (1–4C)alkylthio, (1–4C)alkylsulphinyl, (1–4C)alkylsulphonyl, (2–5C)alkanoyl, carboxy, [(1–4C)alkoxy]carbonyl, [N-(1–4C)alkyl]carbamoyl, (1–5)alkanoylamino and (1–4C)alkyl itself bearing a (1–4C)alkoxy, cyano, carboxy or [(1–4C)alkoxy]carbonyl, and the phenyl optionally bearing a second substituent selected from (1–4C)alkyl, (1–4C)alkoxy, halogeno, trifluoromethyl, nitro and cyano;

or R$^3$ is thienyl or furyl optionally bearing 1 or 2 substituents independently selected from halogeno, (1–4C)alkyl, nitro and cyano; and A$^2$ is (1–6C)alkylene, oxy(1–6C)alkylene or (2–6C)alkenylene, up to three carbon atoms of any of which may be wholly or partially fluorinated, or $A^2$ is a direct bond to $R^3$; or $R^1$ is a group of the formula $Q^2.A^3.Q^1-$, in which: $Q^1$ and $Q^2$ are aromatic moieties, one of which is a benzene moiety and the other of which is a benzene, pyridine or naphthalene moiety, any of which may optionally bear a substituent selected from halogeno, cyano, nitro, (1–4C)alkyl, (1–4C)alkoxy and trifluoromethyl, and $A^3$ is oxy, thio, sulphinyl, sulphonyl, carbonyl, carbamoyl, iminocarbonyl, ureido, (1–6C)alkylene, oxy(1–6C)alkylene, (2–6C)alkenylene or a direct bond between $Q^1$ and $Q^2$;

(b) $R^1$ is pentafluoroethyl and $R^2$ is hydrogen, or both $R^1$ and $R^2$ are trifluoromethyl; or (c) $R^1$ and $R^2$ are both independently alkyl or together form alkylene, such that $R^1$ and $R^2$ together contain 5–9 carbon atoms; and $R^4$ is hydroxy, a physiologically acceptable alcohol residue, or (1–4C)alkanesulphonamido;

or a pharmaceutically acceptable salt thereof.

2. A compound as claimed in claim 1 wherein n and Y have the meanings defined in claim 1, X is hydrogen, hydroxy or methoxy; $A^1$ is methylene, ethylene, trimethylene, tetramethylene or 1,1-dimethylethylene; and:

a) $R^2$ is hydrogen; and $R^1$ is naphthyl, 1-methyl-1-(phenylthio)ethyl or phenylthiomethyl, optionally bearing 1 or 2 substituents selected from fluoro, chloro, bromo, cyano, nitro, methyl, ethyl, methoxy, ethoxy and trifluoromethyl, or $R^1$ is a group of the formula $R^3.A^2-$, in which: $R^3$ is phenyl bearing a substituent which is selected from methyl, ethyl, methoxy, ethoxy, hydroxy, vinly, 2-propenyl, 3,3-dimethylpropenyl, methylthio, ethylthio, methylsulphinyl, ethylsulphinyl, methylsulphonyl, ethylsulphonyl, acetyl, propionyl, butyryl, 2-oxopropyl, carboxy, methoxycarbonyl, ethoxycarbonyl, t-butoxycarbonyl, N-methylcarbamoyl, N-ethylcarbamoyl, N-propylcarbamoyl, formamido, acetamido and propionamido, and from methyl, 1-ethyl, 2-ethyl, 1-propyl, 2-propyl and 3-propyl, any of which alkyl groups itself bearing a methoxy, ethoxy, cyano, carboxy, methoxycarbonyl or ethoxycarbonyl substituent, and the phenyl optionally bearing a second substituent selected from methyl, ethyl, methoxy, ethoxy, fluoro, chloro, bromo, trifluoromethyl, nitro and cyano; or $R^3$ is thienyl or furyl optionally bearing 1 or 2 substituents independently selected from fluoro, chloro, bromo, methyl, ethyl, nitro and cyano; and $A^2$ is methylene, ethylene, trimethylene, isopropylidene, 1,1-dimethylethylene, oxymethylene, oxytetramethylene, 1-oxy-1-methylethyl, 2-oxy-1,1-dimethylethyl, vinylene, 1,3-propenylene or 1,4-buten-2-ylene, up to three carbon atoms of any of which may be wholly or partially fluorinated, or $A^2$ is a direct bond to $R^3$; or $R^1$ is a group of the formula $Q^2.A^3.Q^1-$, in which: $Q^1$ and $Q^2$ are aromatic moieties, one of which is a benzene moiety and the other of which is a benzene, pyridine or naphthalene moiety, any of which may optionally bear a substituent selected from fluoro, chloro, bromo, cyano, nitro, methyl, ethyl, methoxy, ethoxy, trifluoromethyl, and $A^3$ is oxy, thio, sulphinyl, sulphonyl, carbonyl, carbamoyl, iminocarbonyl, ureido, methylene, ethylene, trimethylene, isopropylidene, 1,1-dimethylethylene, vinylene, 1,3-propenylene, 1,4-buten-2-ylene, oxymethylene, oxyethylene or a direct bond between $Q^1$ and $Q^2$;

(b) $R^1$ is trifluoroethyl and $R^2$ is hydrogen, or both $R^1$ and $R^2$ are trifluoromethyl; or (c) $R^1$ and $R^2$ are both independently methyl, ethyl, propyl, isopropyl, butyl or pentyl, or together form tetramethylene, pentamethylene and hexamethylene, any of which may optionally bear 1 or 2 methyl substituents, such that $R^1$ and $R^2$ together contain 5–9 carbon atoms; and $R^4$ is hydroxy, a physiologically acceptable alcohol residue selected from (1–6C)alkyl optionally bearing a hydroxy or (1–4C)alkoxy substituent; phenyl; and benzyl; the latter two of which may optionally bear 1 or 2 optional substituents selected from halogeno, (1–4C)alkyl and (1–4C)alkoxy, or $R^4$ is methanesulphonamido, ethanesulphonamido or butanesulphonamido.

3. A compound as claimed in claim 1 wherein n is 1, X is hydrogen, Y is cis-vinylene, $A^1$ is ethylene, $R^4$ is hydroxy and $R^1$ and $R^2$ are selected from the following combinations:

a) when $R^1$ and $R^2$ are both trifluoromethyl;

b) when $R^1$ is thienyl or furyl, optionally containing a halogeno, cyano or nitro substituent, and $R^2$ is hydrogen;

c) when $R^1$ is phenoxy(1–4C)alkyl, the phenyl moiety of which contains a first substituent selected from (1–4C)alkyl and (1–4C)alkoxy, optionally together with a second substituent selected from (1–4C)alkyl, (1–4C)alkoxy, halogeno, nitro, trifluoromethyl and cyano, and $R^2$ is hydrogen;

d) $R^1$ is phenylthio(1–4C)alkyl, the phenyl moiety of which may optionally bear 1 or 2 substituents independently selected from (1–4C)alkyl, (1–4C)alkoxy, halogeno, nitro, trifluoromethyl and cyano, and $R^2$ is hydrogen;

e) when $R^1$ is naphthyl optionally bearing 1 or 2 substituents selected from halogeno, (1–4C)alkyl and nitro, and $R^2$ is hydrogen; and f) when $R^1$ is benzylphenyl, benzyloxyphenyl, (pyridylmethoxy)phenyl, (naphthylmethoxy)phenyl, phenoxyphenyl and (phenoxymethyl)phenyl.

4. A compound of formula II wherein: $A^4$ is (1–4C)alkylene; $X^1$ is hydrogen or hydroxy; and $R^5$ is naphthyl or thienyl optionally bearing a substituent selected from cyano, nitro, halogeno and (1–4C)alkyl, or $R^5$ is a group of the formula $R^6.A^5-$ in which: $R^6$ is phenyl bearing a first substituent selected from (1–4C)alkyl, (1–4C)alkoxy, hydroxy, (2–5C)alkenyl, (1–4C)alkylthio, (1–4C)alkylsulphinyl, (1–4C)alkylsulphonyl, (2–5C)alkanoyl, carboxy, [(1–4C)alkoxy]carbonyl, [N-(1–4C)alkyl]carbamoyl, (1–5C)alkanoylamino and (1–4C)alkyl, the latter bearing a (1–4C)alkoxy, cyano, carboxy or [(1–4C)alkoxy]carbonyl, said phenyl optionally bearing a second substituent selected from (1–4C)alkyl, (1–4C)alkoxy, halogeno, trifluoromethyl, nitro and cyano, and $A^5$ is (1–4C)alkylene, oxy(1–4C)alkylene or a direct bond to $R^5$; and $R^4$ is hydroxy, a physiologically acceptable alcohol residue, or (1–4C)alkanesulphonamido; or a pharmaceutically acceptable salt thereof.

5. A compound as claimed in claim 4 wherein $A^4$ is ethylene or trimethylene; $X^1$ is hydrogen; $R^4$ is hydroxy, methoxy, ethoxy; and $R^5$ is selected from: 1-naphthyl, 2-naphthyl, 2-chloro-1-naphthyl, 2-thienyl, 3-thienyl, 5-cyano-2-thienyl, 5-bromo-2-thienyl, 4-bromo-2-thienyl, 4-chloro-2-thienyl, 5-chloro-2-thienyl, 2-furyl, 5-bromo-2-furyl, 1-(4-methoxyphenoxy)-1-methylethyl, 1-(4-tert-butylphenoxy)-1-methylethyl, 1-(2-methoxyphenoxy)-1-methylethyl, 1-(2-methylthiophenoxy)-1-methylethyl, 1-(4-methylthiophenoxy)-1-methylethyl, 1-(2-methylsulphonylphenoxy)-1-methylethyl, 1-(4-methylsulphonylphenoxy)-1-methylethyl, 1-methyl-1-(2-methylphenoxy)ethyl, 2-phenylthiophenyl, 2-phenylsulphonylphenyl, 2-biphenylyl, 2-benzoylphenyl, alpha,alpha-difluorobenzyl, 1-methyl-1-(4-methoxy-2-nitrophenoxy)ethyl, 1-methyl-1-(4-methyl-2-nitrophenoxy)ethyl, 1-methyl-1-(2-methyl-6-nitrophenoxy)ethyl, 1-methyl-1-(2-cyano-4-methylphenoxy)ethyl, 1-methyl-1-(4-chloro-2-cyanophenoxy)ethyl, 1-methyl-1-(2-cyano-4-methoxyphenoxy)ethyl, 1-methyl-1-(2-cyano-5-methylphenoxy)ethyl, 1-methyl-1-(2-nitrophenoxy)ethyl, 1-(2-hydroxyphenoxy)-1-methylethyl or (E)-2-methoxystyryl.

6. A compound of the formula II

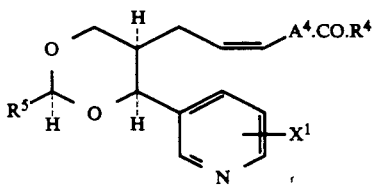

wherein $R^5$ is phenylthio(1–6)alkyl, the phenyl moiety of which may optionally bear 1 or 2 substituents independently selected from (1–4C)alkyl, (1–4C)alkoxy, halogeno, nitro, trifluoromethyl and cyano; $X^1$ is hydrogen or hydroxy; $A^4$ is ethylene or trimethylene: and $R^4$ is hydroxy, a physiologically acceptable alcohol residue selected from (1–6C)alkyl optionally bearing a hydroxy or (1–4C)alkoxy substituent; phenyl; and benzyl; the latter two of which may optionally bear 1 or 2 optional substituents selected from halogeno, (1–4C)alkyl and (1–4C)alkoxy, or $R^4$ is methanesulphonamido, ethanesulphonamido or butanesulphonamido; or a pharmaceutically acceptable salt thereof.

7. A compound of the formula III

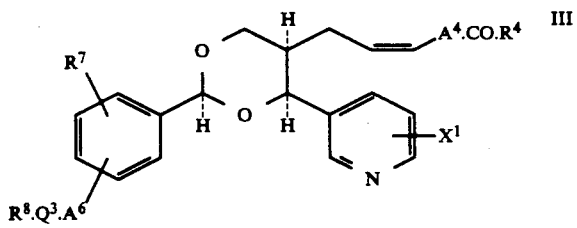

wherein $A^4$ is (1–4C)alkylene; $X^1$ is hydrogen or hydroxy; $A^6$ is oxy, thio, sulphonyl, carbonyl, carbamoyl, iminocarbonyl, (1–6C)alkylene, oxy(1–6C)alkylene or a direct bond to $Q^3$; $Q^3$ is benzene, pyridine or naphthalene; $R^7$ and $R^8$ are independently selected from hydrogen, halogen, cyano, nitro, (1–4C)alkyl, (1–4C)alkoxy and trifluoromethyl; and $R^4$ is hydroxy, a physiologically acceptable alcohol residue, or (1–4C)alkanesulphonamido; or a pharmaceutically acceptable salt thereof.

8. A compound as claimed in claim 7 wherein $A^4$ is ethylene or trimethylene; $X^1$ is hydrogen; $R^4$ is hydroxy, methoxy, ethoxy; $R^7$ is selected from hydrogen, fluoro, chloro, bromo, methyl, ethyl, methoxy, ethoxy, cyano, nitro and trifluoromethyl; and the group of the formula $R^8.Q^3.A^6$— is selected from phenoxy, phenylthio, phenylsulphonyl, phenyl, benzoyl, benzyl, benzyloxy, 4-cyanobenzyloxy, 2-pyridylmethoxy, 3-pyridylmethoxy, 4-pyridylmethoxy, phenoxymethyl, 2-naphthylmethoxy, 2,5-dimethoxybenzyloxy, 4-nitrobenzyloxy and 3-cyanobenzyloxy.

9. A compound as claimed in claim 1, 4, 6 or 7 wherein $R^4$ is hydroxy, X or $X^1$ is hydrogen, and $A^4$ is ethylene.

10. A compound selected from the group consisting of:
4(Z)-6-[(2,4,5-cis)-2-(1-[2-methylphenoxy]-1-methylethyl)-4-(3-pyridyl)-1,3-dioxan-5-yl]hexenoic acid;
4(Z)-6-[(2,4,5-cis)-2-(1-[2-nitro-4-methylphenoxy]-1-methylethyl)-4-(3-pyridyl)-1,3-dioxan-5-yl]hexenoic acid;
4(Z)-6-[(2,4,5-cis)-2-(1-[2-hydroxyphenoxy]-1-methylethyl)-4(Z)-6-[(2,4,5-cis)-2-(1-[2-methylphenoxy]-1-methylethyl)-4-(3-pyridyl)-1,3-dioxan-5-yl]hexenoic acid;
4(Z)-6-[(2,4,5-cis)-2-(1-[2-cyano-4-methylphenoxy]-1-methylethyl)- 4-(3-pyridyl)-1,3-dioxan-5-yl]hexenoic acid;
4(Z)-6-[(2,4,5-cis)-2-(1-[2-cyano-4-methoxyphenoxy]-1-methylethyl)-4-(3-pyridyl)-1,3-dioxan-5-yl]hexenoic acid; and
4(Z)-6-[(2,4,5-cis)-2-(1-[2-nitro-4-methylphenoxy)ethyl]-4-(3-pyridyl)-1,3-dioxan-5-yl]hexenoic acid;
or a physiologically acceptable biodegradable ester or (1–4C)alkanesulphonamide thereof; or a pharmaceutically acceptable salt thereof.

11. A salt as claimed in claim 1 which is selected from the group consisting of alkali metal and alkaline earth metal salts, ammonium salts, salts with organic amines and quaternary bases forming physiologically acceptable cations, and also from salts with acids affording physiologically acceptable anions, such as salts with mineral salts.

12. A method of producing a beneficial effect on the thromboxane $A_2$ system by antagonising one or more of the actions of thromboxane $A_2$ and/or inhibiting its synthesis in a warm-blooded animal which requires such treatment, said method comprising administering to said animal an effective amount of a compound of the formula I, II or III, or a pharmaceutically acceptable salt thereof, as claimed in claim 1, 4, 6 or 7.

13. A pharmaceutical composition which comprises a pharmacologically effective amount of a compound of the formula I, II or III, or a pharmaceutically acceptable salt thereof, as claimed in claim 1, 4, 6 or 7, together with a pharmaceutically acceptable diluent or carrier.

* * * * *

UNITED STATES PATENT AND TRADEMARK OFFICE
CERTIFICATE OF CORRECTION

PATENT NO. : 5,053,415
DATED : October 1, 1991
INVENTOR(S) : Brewster et al

It is certified that error appears in the above-identified patent and that said Letters Patent is hereby corrected as shown below:

Column 43, line 33, (claim 2) correct the spelling of "vinyl".

Column 46, lines 29-32, (claim 10), delete and correctly read the compound as:

--4(Z)-6-[(2,4,5-cis)-2-(1-[2-hydroxyphenoxy]-1-methylethyl)-4-(3-pyridyl-1,3-dioxan-5-yl]hexenoic acid;--

Column 46, lines 39-40, (claim 10), delete and correctly read the compound as:

--4(Z)-6-[(2S,4S,5R)-2-[1-methyl-1-(2-nitro-4-methylphenoxy)ethyl]-4-(3-pyridyl)-1,3-dioxan-5-yl]hexenoic acid;--

Signed and Sealed this

Twenty-second Day of June, 1993

Attest:

MICHAEL K. KIRK

Attesting Officer    Acting Commissioner of Patents and Trademarks